(12) United States Patent
Montgomery, Jr. et al.

(10) Patent No.: US 11,471,092 B2
(45) Date of Patent: Oct. 18, 2022

(54) MICROELECTRODE WITH HEMOGLOBIN OR IRON SENSOR AND METHODS OF GUIDING SAME

(71) Applicant: Greenville Neuromodulation Center, Greenville, PA (US)

(72) Inventors: Erwin B. Montgomery, Jr., Middleton, WI (US); He Huang, Seven Fields, PA (US)

(*) Notice: Subject to any disclaimer, the term of this patent is extended or adjusted under 35 U.S.C. 154(b) by 271 days.

(21) Appl. No.: 15/628,011

(22) Filed: Jun. 20, 2017

(65) Prior Publication Data
US 2017/0360354 A1   Dec. 21, 2017

Related U.S. Application Data

(60) Provisional application No. 62/352,152, filed on Jun. 20, 2016.

(51) Int. Cl.
| | | |
|---|---|---|
| A61B 5/1468 | (2006.01) | |
| A61B 5/00 | (2006.01) | |
| A61B 5/1473 | (2006.01) | |
| A61B 5/145 | (2006.01) | |
| A61B 5/02 | (2006.01) | |
| A61N 1/05 | (2006.01) | |
| A61B 5/24 | (2021.01) | |

(52) U.S. Cl.
CPC ........ *A61B 5/4064* (2013.01); *A61B 5/02042* (2013.01); *A61B 5/1473* (2013.01); *A61B 5/14503* (2013.01); *A61B 5/14546* (2013.01); *A61B 5/7203* (2013.01); *A61B 5/725* (2013.01); *A61B 5/24* (2021.01); *A61B 2562/028* (2013.01); *A61B 2562/063* (2013.01); *A61N 1/0534* (2013.01)

(58) Field of Classification Search
CPC ..... A61B 5/4064; A61B 5/725; A61B 5/7203; A61B 5/14546; A61B 5/14503; A61B 5/1473; A61B 5/4836; A61B 5/04001; A61B 2562/028; A61B 2562/063; A61B 5/02042; A61N 1/0534
See application file for complete search history.

(56) References Cited

U.S. PATENT DOCUMENTS

| | | |
|---|---|---|
| 7,136,696 B2 | 11/2006 | Montgomery, Jr. |
| 7,957,793 B2 | 6/2011 | Montgomery, Jr. et al. |
| 8,150,795 B2 | 4/2012 | Montgomery, Jr. et al. |

(Continued)

FOREIGN PATENT DOCUMENTS

WO   2011028608 A2   3/2011

OTHER PUBLICATIONS

Toh et al. Direct In Vivo Electrochemical Detection of Haemoglobin in Red Blood Cells. Scientific Reports, DOI: 10. 1038/srep06209 (Year: 2014).*

(Continued)

*Primary Examiner* — Christian Jang
(74) *Attorney, Agent, or Firm* — The Webb Law Firm

(57) ABSTRACT

Provided herein are microelectrodes and methods of localizing and targeting the same. The microelectrodes include electrochemical or biological sensors, an array of electrical contacts along a long axis of the microelectrode, or both. The methods of localizing and targeting use statistical manipulations to reduce the errors inherent in spike train analyses.

18 Claims, 28 Drawing Sheets

(56) References Cited

U.S. PATENT DOCUMENTS

| | | | | |
|---|---|---|---|---|
| 2003/0201177 | A1* | 10/2003 | Hodges | C12Q 1/006 204/403.01 |
| 2007/0123765 | A1* | 5/2007 | Hetke | A61B 5/04001 600/378 |
| 2008/0269582 | A1* | 10/2008 | Mansour | A61B 5/14542 600/357 |
| 2011/0257496 | A1* | 10/2011 | Terashima | A61B 5/14532 600/347 |
| 2013/0123600 | A1* | 5/2013 | Tcheng | A61B 5/0261 600/378 |
| 2015/0265194 | A1* | 9/2015 | Pollonini | A61B 5/14546 600/301 |
| 2016/0051812 | A1 | 2/2016 | Montgomery, Jr. et al. | |

OTHER PUBLICATIONS

Chao et al., "A MoS2-based system for efficient immobilization of hemoglobin and biosensing applications", Nanotechnology, 2015, 9 pp., vol. 26.

Chenkin et al., "Direct electrochemistry and bioelectrocatalysis of a class II non-symbiotic plant haemoglobin immobilised on sceen-printed carbon electrodes", Analytical and Bioanalytical Chemistry, 2010, pp. 1643-1649, vol. 398.

Dengler et al., "Microfabricated Microelectrode Sensor for Measuring Background and Slowly Changing Dopamine Concentrations", Journal of Electroanalytical Chemistry, 2013, pp. 28-33, vol. 693.

Li et al., "Determination of traces of hemoglobin by square wave stripping voltammetry at a silver microelectrode", Fresenius' Journal of Analytical Chemistry, 1996, pp. 359-360, vol. 356.

Li, "A Spirally-rolled Flexible Polymer Tube Integrated with Microsensors and Microfluidic Devices for Multifunctional Smart Microcatheters" Dissertation, University of Cincinnati, 2007, 174 pp.

Liu et al., "Direct electron transfer and electrochemical study of hemoglobin immobilized in ZnO hollow spheres", Bioprocess and Biosystems Engineering, 2011, pp. 931-938, vol. 34.

Montgomery, Jr. et al., "Methods for isolating extracellular action potentials and removing stimulus artifacts from microelectrode recordings of neurons requiring minimal operator intervention", Journal of Neuroscience Methods, 2005, pp. 107-125, vol. 144.

Sun et al., "Preparation of hemoglobin (Hb) imprinted polymer by Hb catalyzed eATRP and its application in biosensor", Biosensors and Bioelectronics, 2016, pp. 894-900, vol. 77.

Takeshita et al., "Analyzing spike trains with circular statistics", American Journal of Physics, 2009, pp. 424-429, vol. 77.

Wang et al., "Electrochemical Biosensors Based on Ferroceneboronic Acid and Its Derivatives: A Review", Biosensors, 2014, pp. 243-256, vol. 4.

Yang et al., "Interdigitated Array Microelectrode-Based Electrochemical Impedance Immunosensor for Detection of *Escherichia coli* O157:H7", Analytical Chemistry, 2004, pp. 1107-1113, vol. 76.

Zhao et al., "The interface behavior of hemoglobin at carbon nanotube and the detection for H2O2", Talanta, 2005, pp. 489-494, vol. 65.

* cited by examiner

Spike train 1 regular

Spike train 2 least irregular

Spike train 3 irregular

Spike train 4 irregular

Spike train 5 irregular

Spike train 6 irregular

Spike train 7 most irregular

Spike train 8 bursting

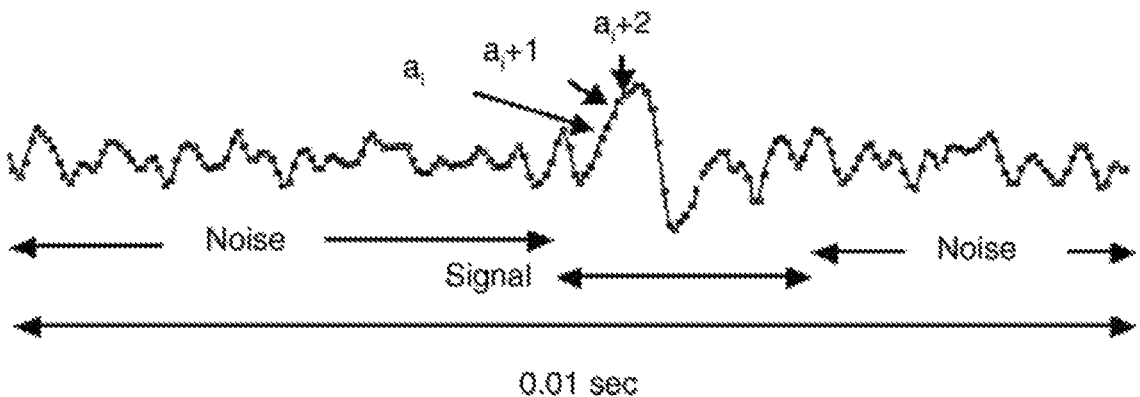
Analysis based on regression towards the mean
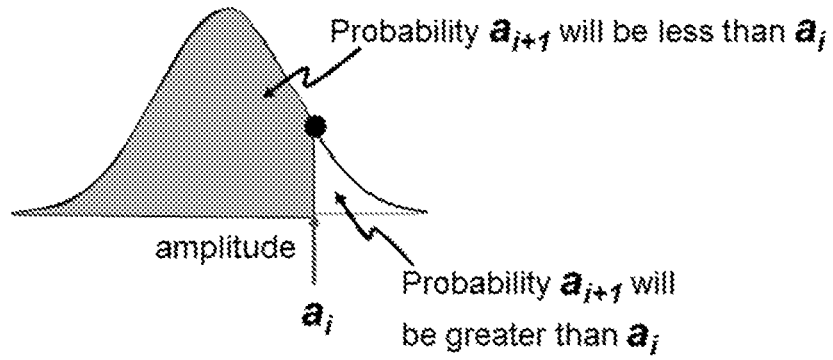
As $a_j$ increases the probability that $a_{j+1}$ will be less than gets less
As $a_j$ increases the probability that $a_{j+2}$ will be less than gets less
This relation used because of digitization noise
FIG. 5A – Prior Art

MICROELECTRODE WITH HEMOGLOBIN OR IRON SENSOR AND METHODS OF GUIDING SAME

CROSS REFERENCE TO RELATED APPLICATION

The present application claims the benefit of U.S. Provisional Patent Application No. 62/352,152, filed Jun. 20, 2016, the content of which is incorporated by referenced herein in its entirety.

BACKGROUND OF THE INVENTION

Field of the Invention

The present invention relates to electrodes for recording electric potentials in the brain. More particularly, the present invention relates to microelectrodes for recording extracellular action potentials, with specific sensors for detecting hemoglobin and/or iron.

The present invention also relates to methods for guiding a microelectrode in the brain. More particularly, the present invention also relates to manipulations of recorded electrical activity sensed by microelectrodes to provide more sensitive and accurate detection of extracellular action potentials and action potential trains, and increased ability to filter noise and artifacts.

Description of Related Art

The primary purpose of target localization is to identify within a three-dimensional space the region in which deep brain stimulation (DBS) will produce optimal benefit. Additional targets must be identified and avoided, lest stimulation produce adverse effects. The primary targets for efficacy in the globus pallidus interna (GPi) and the ventral intermediate nucleus of the thalamus (Vim) are the appropriate homuncular representation within sensorimotor regions. With respect to the subthalamic nucleus (STN), it is just the sensorimotor region. Primary targets to be avoided include the posterior limb of the internal capsule in both the GPi, STN, and Vim; the optic tract in GPi; and the medial lemniscus and oculomotor nerve roots in STN DBS. To date, microelectrode recordings (MERs) of extracellular action potentials are the only effective mechanism.

MERs in the nervous system allows analysis of neuronal activities in order to identify the optimal target for therapeutic intervention. In the case of DBS therapies, the intervention requires the permanent implantation of electrodes to provide electrical stimulation to treat disorders. Other therapeutic interventions can include systems for delivery of drugs and biologics such as but not limited to genes, cells, and drugs with or without permanent delivery devices.

Not infrequently during MER, situations are encountered where no neuronal activity is discernable. The question arises as to whether the patient had an intracerebral hematoma. To determine the cause of the signal loss, surgeries have previously been aborted to obtain a CT scan to determine whether intracranial bleeding has occurred, a process that is time consuming and not desirable. Accordingly, there is a need in the art for a microelectrode that can assist in identifying or discerning a hematoma or other critical situation from other situations that may arise during MERs.

One of the most important uses of intraoperative neurophysiological monitoring (IONM) using MERs is the identification of anatomical/physiological targets for surgical intervention as well as demonstrating any changes in the integrity of physiological systems that may be affected during the course of surgery. In the case of DBS lead implantation surgery, the typical purpose is to identify a trajectory through the brain for the placement of the permanent DBS lead. Typically, the best trajectory would be defined by those properties that best directly predict optimal clinical outcome. Unfortunately, there is no known set of properties that directly predict clinical outcome, for many reasons the review of which is beyond the scope of this manual. Consequently, a series of proxies are used which can include: 1) position relative to the internal landmarks of the anterior and posterior commissures; 2) direct anatomical visualization of the target structure, for example, the subthalamic nucleus (STN), globus pallidus interna (GPi) and the ventral intermediate nucleus of the thalamus (Vim); and 3) identification based on electrophysiological properties. Each of these approaches have advantages and disadvantages, for example in invasiveness, cost such as duration of surgery, and the consequences of DBS lead misplacement.

In identifying the physiological targets to be stimulated and those to be avoided, it is necessary that whatever means is employed, one of two approaches may be taken. First, the measures employed must distinguish the targets from their adjacent structures. For example, in the case of the STN, whatever method used must be able to distinguish the sensor-motor region of the STN from the limbic and cognitive regions of the STN. To date, there is no neuroimaging/anatomical technique that can make such a distinction. By contrast, microelectrode recordings (MERs) can make the distinction. For a patient with cervical dystonia, whatever methods used it must be able to distinguish the head homuncular representation in the sensori-motor region from the other parts of the body. Again, to date there is no neuroimaging/anatomical technique that can make such a distinction whereas MER can. However, it is important to note that MERs are conducted following neuroimaging based targeting and the best guarantee of successful MER is optimal neuroimaging based targeting.

The other approach is to utilize proxies for the actual physiological targets described above. For example, it may well be that the physiological target has a fixed relationship to anatomical structures that can be visualized by other methods such as MRI or CT scans. For example, one could use a fixed spatial relation to the midpoint of a line connecting the anterior and posterior commissures. Alternatively, one could target a specific anatomical region of the directly visualized anatomical structure, for example the dorsal and lateral region of the STN, or the GPi as it abuts on the posterior limb of the internal capsule.

The benefit of automating the process of MER (creating an aaMER system), such as described herein, is twofold. First, it is to optimize the current practice of IONM for DBS lead implantation surgery. There still are numerous aspects of the procedures that are highly subjective, for example, answering the question whether there are signals representative of the electrical activity of individual neurons contained in the MERs. The subjective nature of some processes has two important consequences. First, it necessitates a long apprenticeship to gain the necessary experience to make effective subjective decisions. Second, subjectivity, even in the hands of well-meaning experts still results in preventable errors.

The second motivation for aaMER systems is to reduce the obstacles for patients seeking DBS therapy. The number of experts in IONM is limited and insufficient. This has two consequences. First, patients just don't get access to DBS.

Second, in seeking to provide DBS, surgeons may compromise and use methods that do not provide the highest probability of optimal outcome. The second consequence carries with it a social hazard. Using these other methods that do not require the same level of expertise could result in less efforts to obtain the optimal level of expertise necessary to employ methods most likely to provide optimal outcomes. In the face of the paucity of IONM experts for DBS, aaMER systems provide the possibility of experts being involved remotely. An effective aaMER system would mean that geography is no longer a barrier to the most optimal therapy. With an effective aaMER system in place combined with complete turnkey stereotactic surgery solutions such as prefabricated microdrive frames or platforms, nearly any operating room staffed by a neurosurgeon could offer DBS.

To meet the need for optimal targeting, MERs must be capable of recognizing the spikes generate by individual neurons. This necessity imposes very important requirements on any MER system. For example, it generally is easier to record from semi-microelectrodes due to the relatively lower electrode impedances. However, the result is a plethora spikes making it very difficult to isolate spikes referable to any single neuron. The implications of this inability to isolate spikes referable to individual neurons is discussed elsewhere in this manual.

Once the ability of recording and discriminating spikes referable to individual neurons is secured, it is relatively straight forward, though not unproblematic, to demonstrate sensori-motor driving and the homuncular representation. But this alone is not sufficient. A critical issue for DBS clinical efficacy is the ability to activate a sufficient volume of brain tissue but not so much as activate other nearby structures whose adverse consequences would limit benefit. Identifying a single neuron sensori-motor driven by manipulation of the appropriate body part would not be sufficient as it does not answer how large a volume of appropriate brain activation would be accomplished with the placement of the DBS lead at the location of the single neuron. Consequently, for example, one criteria often used is that the trajectory contains 5 mm of tissue containing sensori-motor driven neurons in the case of the STN.

Just determining whether the trajectory of MERs identifies the optimal trajectory for the DBS lead frequently is insufficient. If the criteria is not met by the current trajectory, in which way should one move to most efficiently find the trajectory that will meet the criteria? To that question, far more information is required. This means that one must know the regional anatomy around the trajectory. For example, a trajectory to the STN that identifies a region referable to the ventral posterior oralis thalamus (Vop) would be a strong indication that the trajectory is too posterior. Failure to identify neuronal activities of the substantia nigra pars reticulata (SNr) might suggest that the trajectory is in medial GPi due to severe brain shift, rather than in STN. Encountering the neuronal activities indicative of the STN very high in the trajectory and for only a small length would indicate that the trajectory may be too lateral. One important implication is that surgeons, for the sake of reducing OR time, starting the MER just above the STN will miss important information to direct a move should the trajectory being studied be found not to meet the criteria for an optimal trajectory.

The regional anatomy surrounding the trajectory can only be inferred from the electrophysiological properties of individual neurons. Among the criteria used are the relative density of neurons at an MER site, spike frequencies, patterns in the spike train and unique spike waveforms. This means that it is necessary to discriminate among the spikes which are referable to individual neurons in order to estimate the number of neurons present. An electrode whose tip is too large, and consequently the impedance is too low, would not allow an estimation of the neuronal density, spike frequency, spike train patterns or spike waveforms.

The human brain, with sufficient training and practice, can be very good at identifying a signal within the MER indicative of a neuronal spike. However, inter-observer variation complicates the matter and introduces an element of variability that increases the risk associated with MER. Accordingly, a need exists in the art for an automated MER analysis that removes the subjective variable from target localization.

SUMMARY OF THE INVENTION

Provided herein is a microelectrode including a body having a proximal end, a distal end, and a sidewall there between defining a longitudinal axis. The body includes an electrically non-conductive material and at least one portion comprising an electrically conductive material. The microelectrode further includes at least one electrochemical or biological biosensor disposed within or on the body.

In aspects, the at least one electrochemical or biological biosensor is an iron sensor. In further aspects, the iron sensor is an iron (II) or iron (III) sensor. In other aspects the at least one electrochemical or biological biosensor is a hemoglobin sensor.

In some aspects, the at least one electrochemical or biological biosensor is at least two electrochemical or biological biosensors. In further aspects, where the at least one electrochemical or biological sensor is at least two electrochemical or biological biosensors, the sensors are disposed along at least 1 mm of the longitudinal axis of the body, preferably at least 2 mm, more preferably at least 5 mm, most preferably at least 10 mm.

In aspects of the microelectrode, the microelectrode comprises a tip at the distal end. In some aspects the tip is a frustoconical shape. In further aspects, the tip is a cone shape.

In aspects, the at least one portion comprising an electrically conductive material is the tip. In some aspects, the electrically non-conductive material is an organic or inorganic polymer, ceramic, or glass. In further aspects, the electrically non-conductive material is glass.

In some aspects, the electrically conductive material is a metal or a carbon fiber material. In further aspects, the electrically conductive material is at least one of stainless steel, aluminum, copper, graphite, platinum, gold, palladium, iridium, ruthenium, tungsten, alloys thereof, and combinations thereof. In further aspects, the electrically conductive material is at least one of tungsten and a platinum-iridium alloy. In some other aspects, the electrically conductive material is an electrically conductive polymer.

In some aspects, the body of the microelectrode includes an electrically conductive material and the electrically non-conductive material is an insulating material covering substantially the entire body. In further aspects, the insulating material is a polyurethane or a polyimide.

Also provided herein is a method of detecting the presence of a hematoma in a patient's brain during neurophysiological monitoring, including the steps of advancing a microelectrode as described above along a path within the brain of a patient and detecting, with the at least one electrochemical or biological biosensor, the presence or absence of a chemical or biological analyte, wherein the presence of the chemical or biological analyte is indicative of the presence of a hematoma.

In some aspects, the at least one electrochemical or biological biosensor of the microelectrode is an iron sensor. In further aspects, the iron sensor is an iron (II) or iron (III) sensor.

In other aspects, the at least one electrochemical or biological biosensor of the microelectrode is a hemoglobin sensor.

In some aspects, the at least one electrochemical or biological biosensor is at least two electrochemical or biological biosensors. In further aspects, where the at least one electrochemical or biological sensor is at least two electrochemical or biological biosensors, the sensors are disposed along at least 1 mm of the longitudinal axis of the body, preferably at least 2 mm, more preferably at least 5 mm, most preferably at least 10 mm.

In aspects of the method, the process further includes the step of advancing the electrode after detection of the chemical or biological analyte until the chemical or biological analyte is not detected, thereby providing an indication of the size of the hematoma.

Also provided herein is a method of localizing a microelectrode within the brain of a patient, including the steps of advancing a microelectrode, in some aspects an electrode as described above, along a path within the brain of a patient, detecting, with the microelectrode, two or more extracellular action potentials, and analyzing, with at least one processor, the extracellular action potentials over a time period. The analysis includes the steps of transforming, with at least one processor, the time period to a circle, transforming, with at least one processor, the extracellular action potentials to unit vectors extending outward from a perimeter of the circle, calculating, with at least one processor, a resultant vector having a length (r) and an angle (θ), the length and angle dependent on the unit vectors, calculating, with at least one processor, a change in r and θ of the resultant vector over time, calculating, with at least one processor and using a peak detection algorithm, power spectral density (PSD) peaks of the change in r and θ of the resultant vector over time, calculating, with at least one processor, a mean height of PSD peaks corresponding to change in r and half-height widths of PSD peaks corresponding to change in r and change in angle. The method further includes the steps of determining, with at least one processor and based on the mean height and half-height widths, an anatomical location of the microelectrode, and storing, in a database, the mean height, half-height widths, and anatomical location.

Also provided herein is a microelectrode including a body having a proximal end, a distal end, and a sidewall therebetween defining a longitudinal axis, the body including an electrically non-conductive material and at least one electrical contact comprising an electrically conductive material, said electrical contact embedded in a cavity in the sidewall of the body and configured such that the electrical contact does not protrude radially beyond the perimeter of the body. In some aspects, the electrical contact is a conical shape.

In aspects, the electrical contact occupies less than the entirety of the cavity in the sidewall. In further aspects, the remaining space in the cavity is filled with a porous material. In some further aspects, the porous material is a cotton fiber, glass sponge, ceramic, gel, plastic, or collodion. In aspects, the porous material is wetted with a conductive substance. In further aspects, the conductive substance is physiological saline, other biologically compatible solution containing ions, or artificial cerebrospinal fluid.

In aspects, the electrical contact is embedded in a non-conductive material that extends radially outward from the body of the microelectrode.

In aspects, the microelectrode further includes one or more sensors for detecting hemoglobin or iron.

Also provided herein is a method of localizing a microelectrode within the brain of a patient, including the steps of advancing a microelectrode as described above along a path within the brain of a patient, detecting, with the at least one electrical contact of the microelectrode, two or more extracellular action potentials, and analyzing, with at least one processor, the extracellular action potentials over a time period. The analysis includes the steps of transforming, with at least one processor, the time period to a circle, transforming, with at least one processor, the extracellular action potentials to unit vectors extending outward from a perimeter of the circle, calculating, with at least one processor, a resultant vector having a length (r) and an angle (θ), the length and angle dependent on the unit vectors, calculating, with at least one processor, a change in r and θ of the resultant vector over time, calculating, with at least one processor and using a peak detection algorithm, power spectral density (PSD) peaks of the change in r and θ of the resultant vector over time, and calculating, with at least one processor, a mean height of PSD peaks corresponding to change in r and half-height widths of PSD peaks corresponding to change in r and change in angle. The method further includes the steps of determining, with at least one processor and based on the mean height and half-height widths, an anatomical location of the microelectrode and storing, in a database, the mean height, half-height widths, and anatomical location.

Also provided herein is a method of localizing a microelectrode within the brain of a patient, including the steps of advancing a microelectrode described above along a path within the brain of a patient, the microelectrode in communication with at least one processor, detecting, with the at least one electrical contact of the microelectrode, two or more extracellular action potentials, and analyzing, with at least one processor, the extracellular action potentials over a time period. The analysis includes the steps of determining, with at least one processor, an interval between two action potentials, calculating, with at least one processor and based on the determined interval, a mean interval between action potentials, and calculating, with at least one processor, an absolute value of a difference between the determined interval and the mean interval, normalizing, with at least one processor, the absolute value. The method further includes the steps of determining, with at least one processor and based on the normalized absolute value, an anatomical location of the microelectrode and storing, in a database, the normalized absolute value and anatomical location of the microelectrode.

BRIEF DESCRIPTION OF THE DRAWINGS

FIGS. 5A-5B shows a prior art method of determining threshold and probability that a detected electrical signal is a neuronal spike train rather than noise or artifact. Distribution of the probabilities that $a_{i+2}$ will be greater than $a_i$ for the actual MER in blue and following randomization of the order of the voltage amplitudes in red. As can be seen, the blue distribution has three peaks. The central peak is due to noise and the two side peaks represent the effects of the positive and negative peaks in the neuronal spikes. The red distribution shows the effects of just noise due to the randomization of the order of the voltage amplitudes. The amplitude of $a_i$ where the two distributions do not overlap indicates the threshold where amplitudes greater than the threshold indicate amplitudes belonging to the neuronal spikes while amplitudes less than the threshold represent amplitudes attributable to noise for the positive signals. The converse is applied to negative signals to determine the negative threshold for detecting neuronal spikes.

DETAILED DESCRIPTION OF THE INVENTION

Figure 1A:
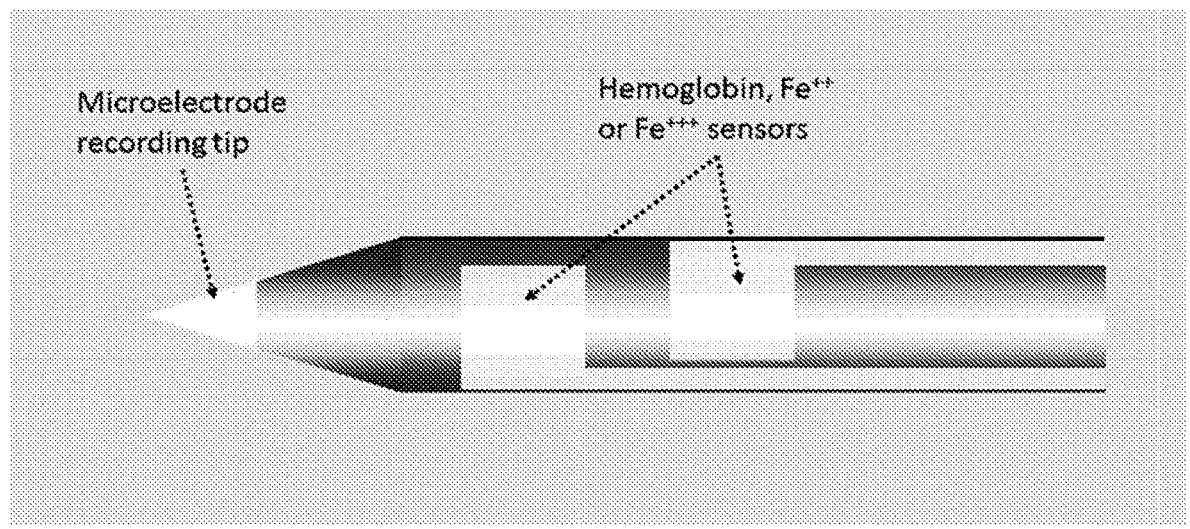
FIGS. 1A-1D shows a schematic representation of aspects of a microelectrode according to the present invention; (1A) a microelectrode with a hemoglobin or iron sensor according to one aspect of the present invention; (1B) a schematic of designs for electrical contacts for microelectrodes according to one aspect of the present invention; (1C) a schematic representation of a microelectrode with an array of electrical contacts according to one aspect of the present invention; and (1D) a schematic of various electrode array designs, according to one aspect of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

The figures accompanying this application are representative in nature, and should not be construed as implying any particular scale or directionality, unless otherwise indicated.

Described herein are microelectrodes including a hemoglobin or iron sensor for aiding in the detection of a, for example, hematoma within the brain. The microelectrode includes a body having a proximal end, a distal end, and a sidewall therebetween defining a longitudinal axis. The body includes an electrically non-conductive material and at least one portion including an electrically conductive material, to serve as an electrical contact.

Suitable conductive materials for use in the microelectrodes according to one aspect of the present invention include, for example tungsten, stainless steel, platinum, iridium and iridium oxide, aluminum, copper, graphite, gold, palladium, ruthenium, alloys thereof, and combinations thereof. In some aspects, the electrical contact of the microelectrode is formed of at least one of tungsten and a platinum-iridium alloy. An electrical contact for a microelectrode as described herein can also be formed of an electrically-conductive polymer.

Suitable non-conductive materials for use in a microelectrode according to an aspect of the present invention can be glass and non-conductive polymers. In some embodiments, the body of the microelectrode is formed substantially from one of the aforementioned conductive materials, and includes a non-conductive coating or layer thereon. This non-conductive coating can be substantially or completely non-conductive. In some embodiments, the non-conductive coating is an insulating coating that is substantially or completely non-conductive, and substantially covers the electrically-conductive material that makes up the electrical contacts.

In some aspects, the microelectrode includes an electrical contact at the distal end of the microelectrode body, and includes multiple sensors arranged over a length of the shaft of the microelectrode, proximal of the electrical contact. While FIG. 1A shows the hemoglobin or iron sensors as located proximally of a tapered distal end of the electrical contact (microelectrode recording tip in FIG. 1A), those of skill will appreciate that the biological/chemical/electrochemical sensors for hemoglobin/iron can be located at any portion along the microelectrode, that is useful for determining the presence and size of a hematoma.

As described herein, not infrequently during MER, situations are encountered where no neuronal activity is discernable. The question arises as to whether the patient had an intracerebral hematoma, which can be a critical situation. As used herein, the term "patient" refers to members of the animal kingdom including but not limited to mammals and human beings and is not limited to humans or animals in a doctor-patient or veterinarian-patient relationship. "A patient" refers to one or more patients such that a treatment effective in "a patient" refers to a treatment shown effective in one patient or a statistically significant number of patients in a population of patients.

To determine the cause of the loss of activity during MER, surgeries are typically aborted, so that a CT scan (or other imaging procedure) can be taken to determine whether intracranial bleeding has occurred. Because such actions are time consuming, also included in the microelectrode, according to one aspect of the present invention is one or more electrochemical or biological sensors, disposed within or on the surface of the microelectrode body. In some aspects, the electrochemical or biological sensor is one or more hemoglobin or iron sensors. In some aspects a number of hemoglobin and/or iron sensors are arrayed over, for example, in the range of about 10 mm of the length of the microelectrode, in order to determine the spatial extent of a hematoma, in order to differentiate a clinically insignificant hematoma from a significant intracranial hematoma. In some embodiments the sensors include 2 or more, 3 or more, 4 or more, 5 or more, 6 or more, 7 or more, 8 or more, 9 or more, or 10 or more, located over a range of 1 mm or more, 2 mm or more, 3 mm or more, 4 mm or more, 5 mm or more, 6 mm or more, 7 mm or more, 8 mm or more, 9 mm or more, or 10 mm or more of the shaft of the microelectrode.

In aspects, the microelectrode described herein according to one aspect of the present invention integrates a hemoglobin sensor and/or an $Fe^{2+}$ or $Fe^{3+}$ sensor, electrochemical or biological, into the microelectrode to determine whether there is a hematoma.

With reference to FIG. 1A, shown is a schematic representation of a microelectrode for recording neuronal activities through the tip and sensors of hemoglobin, $Fe^{2+}$ and/or $Fe^{3+}$ in the adjacent tissue. As shown in FIG. 1A, multiple sensors can be arrayed along the long axis of a microelectrode to determine the spatial extent and thus, clinical significance of any intracerebral hematoma. The microelectrode can include one or multiple different types of sensors, arrayed along a given portion of the microelectrode shaft. Sensors for detecting hemoglobin and/or various oxidation forms of iron can be prepared according to known methods, for example as described in Sun et al. "Preparation of hemoglobin (Hb) imprinted polymer by Hb catalyzed eATRP and its application in biosensor." *Biosens Bioelectron.* 2016; 77: 894-900 (published ahead of printing on Oct. 26, 2015), Wang et al. "Electrochemical biosensors based on ferroceneboronic Acid and its derivatives: a review." *Biosensors (Basel).* 2014; 4(3): 243-56, and Chekin et al. "Direct electrochemistry and bioelectrocatalysis of a class II non-symbiotic plant haemoglobin immobilised on screen-printed carbon electrodes." *Anal Bioanal Chem.* 2010; 398 (4): 1643-9, each of which is incorporated herein by reference in their entirety.

In addition, microelectrodes can be prepared according to known methods. For example, and without limitation, a microelectrode can be formed substantially as shown in FIG. 1A. That is, a microelectrode according to the present invention can include a shaft, a distal end, and a proximal end (not shown in FIG. 1A). A recording tip, or electrical contact, including an electrophysiological sensor, can be provided at the distal end of the microelectrode, as shown in FIG. 1A. The microelectrode includes one or more hemoglobin and/or iron sensors, arranged along the shaft of the microelectrode.

While depicted in FIG. 1A as parallelograms, the sensors of the microelectrode described herein can be of any useful shape, for example circular, triangular, or trapezoidal patches, rings that extend around the circumference of the shaft, and the like.

The microelectrode as described herein can also include a lumen through the shaft (not shown in FIG. 1A), defined by a shaft wall, which lumen can include or allow for passage of one or more components of the microelectrode recording tip and the sensors. In embodiments, the sensors are provided on the shaft wall of the microelectrode and, for example, connectors, wiring, and the like passes through the lumen of the microelectrode. In other embodiments, the body of the electrode is conductive, formed from a conductive material as described herein, including a lumen, and includes a non-conductive coating thereon. In this way, there is no separate electrophysiological sensor at the distal end of the electrode. Rather, the electrode itself, formed of a conductive material, acts as the electrophysiological sensor for detecting action potentials. Biological/chemical/electrochemical sensors (for detection of hemoglobin and/or iron) are arranged as described previously. In still other embodiments, the electrode itself is formed of a non-conductive material, and the distal end, for example and without limitation, the tip, includes an electrophysiological sensor, for example a conductive portion formed from a conductive material as described above. No matter the construction of the body, or the electrophysiological sensor, a microelectrode according to the present invention includes one or more hemoglobin and iron sensors along the shaft.

Microelectrodes can be purchased commercially, and modified to include biological/chemical/electrochemical sensors for hemoglobin and/or iron as described herein. Commercial sources for such microelectrodes include, for example, FHC (Bowdoin, Me.), World Precision Instruments (Sarasota, Fla.), and Thomas Recording (Giessen, Germany).

In addition to the aspect of the present invention including a microelectrode with a hemoglobin and/or iron sensor included along the shaft, also provided herein is a microelectrode with a number of electrical contacts arrayed along the long axis thereof for providing a more spatially-accurate representation of action potentials. Note that these aspects (electrochemical and/or biological sensors and an array of electrical contacts need not be exclusive of each other. That is, in aspects, a microelectrode according to the present invention can include one or both of a hemoglobin or iron sensor and an array of electrical contacts as will be further described herein.

The use of more than one electrical contact or electrode can increase the speed with which DBS implantation surgery can be performed. For example, moving a single microelectrode through a 20 mm trajectory may take 40 minutes. However, moving 10 contacts in a linear array arranged at 2 mm intervals would require only a fraction of the time to cover the 20 mm trajectory. The major problem is that the geometry of the electrical contacts are planar which is not optimal for recording extracellular action potentials.

Figure 1B:
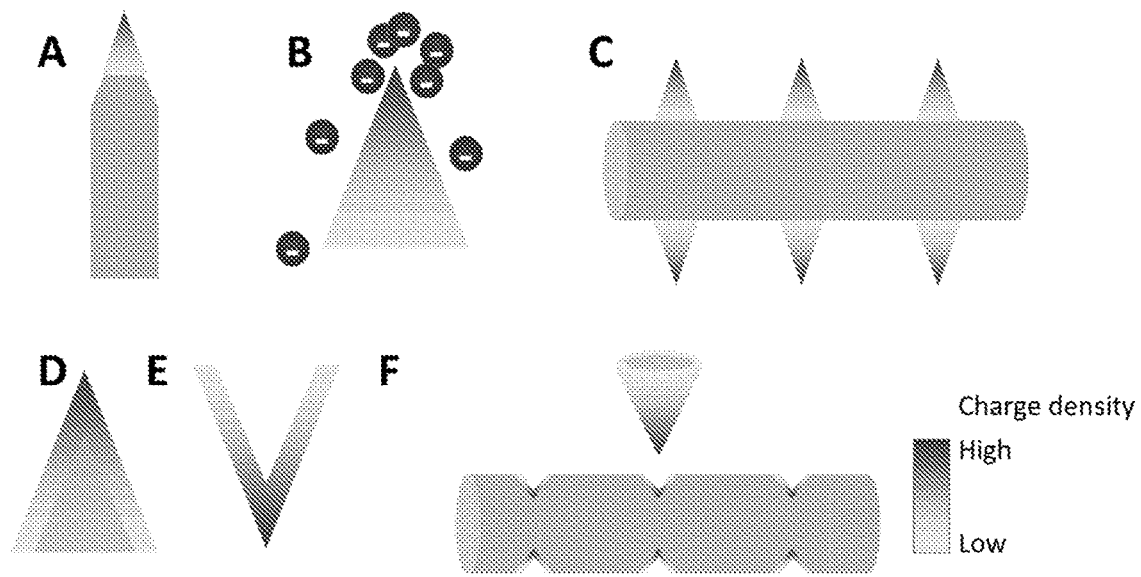

Thus, in an aspect of the present invention, electrical contacts are configured to provide a point, whether extending radially outward or radially inward, to provide a location at which density of electric charge can be focused and maximized (FIG. 1B, panel B). Typically, this might take the form of a point, for example as shown in FIG. 1A and FIG. 1B, panel A where the "front" of the microelectrode comes to a point (though this "point" need not be a sharp point as shown in FIG. 1A). However, there is a risk of tissue damage as a microelectrode with such a point (again, sharp or otherwise) moves through tissue. To take advantage of the benefits of electrical contacts with such "points", and to provide better spatial resolution and accuracy, numerous electrical contacts could be arrayed along the length of a microelectrode, such as shown in FIG. 1B, panel C. However, just as with a microelectrode shown in FIG. 1A and FIG. 1B, panel A where the "front" of the microelectrode comes to a point, the microelectrode shown in FIG. 1B, panel C, would cause unwanted damage to tissue as the electrode moved through the body.

Figure 1C:
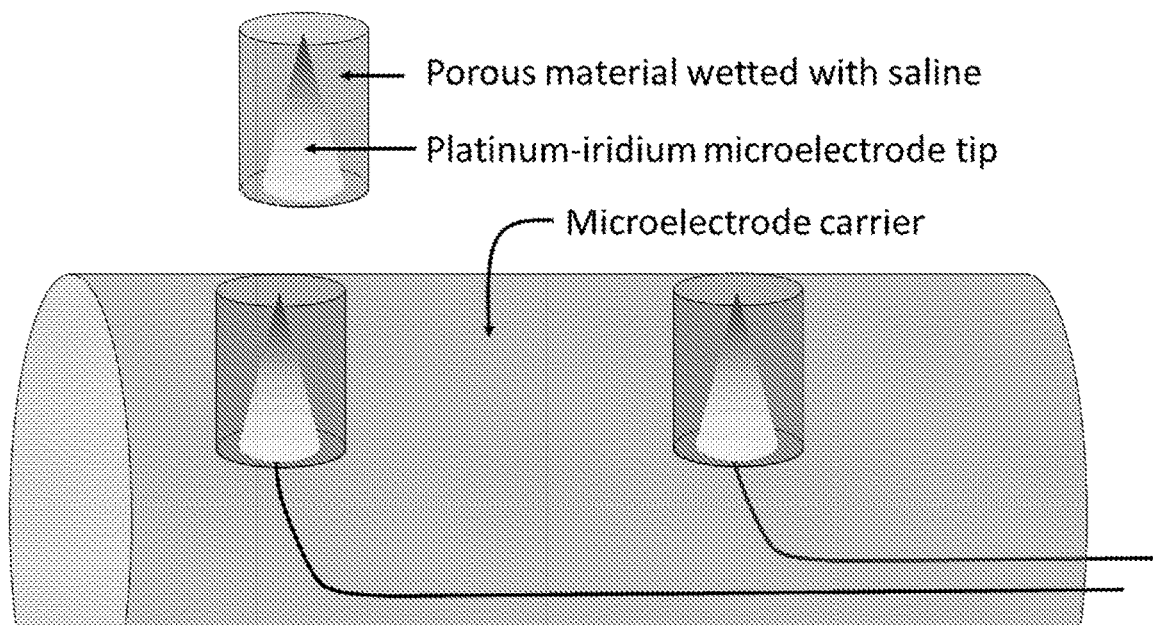

To this end, and again to take advantage of the benefits of such a "point", an electrode according to one aspect of the present invention can include an array of electrical contacts embedded in the sidewall of an electrode body, such as shown in FIG. 1B, panel F and FIG. 1C. By embedding the electrodes in the sidewall, the cross-section of the electrode body itself need not change in diameter or shape, such that there would be no "pointed" electrical contacts extending radially outward from the electrode body itself. Thus, the benefits of a pointed contact, in terms of density of charge, can be realized without the concomitant tissue damage that might be expected from an electrode configured such as shown in FIG. 1B, panel C.

In one aspect of the present invention, the electrodes are arranged substantially as shown in FIG. 1B, panel F, that is, with the "point" for increased charge density located radially inward of a perimeter of the electrode body itself. In another aspects, the electrodes are arranged substantially as shown in FIG. 1C, that is with the "point" for increased charge density located near the perimeter of the electrode body itself. No matter the configuration, the use of such "pointed" electrodes allows for creating maximum charge densities.

In some aspects, a number of electrical contacts are arrayed over, for example, in the range of about 10 mm of the length of the microelectrode, in order to determine the spatial extent of a hematoma, in order to differentiate a clinically insignificant hematoma from a significant intracranial hematoma. In some embodiments the sensors include 2 or more, 3 or more, 4 or more, 5 or more, 6 or more, 7 or more, 8 or more, 9 or more, or 10 or more, located over a range of 1 mm or more, 2 mm or more, 3 mm or more, 4 mm or more, 5 mm or more, 6 mm or more, 7 mm or more, 8 mm or more, 9 mm or more, or 10 mm or more of the shaft of the microelectrode.

Figure 1D:
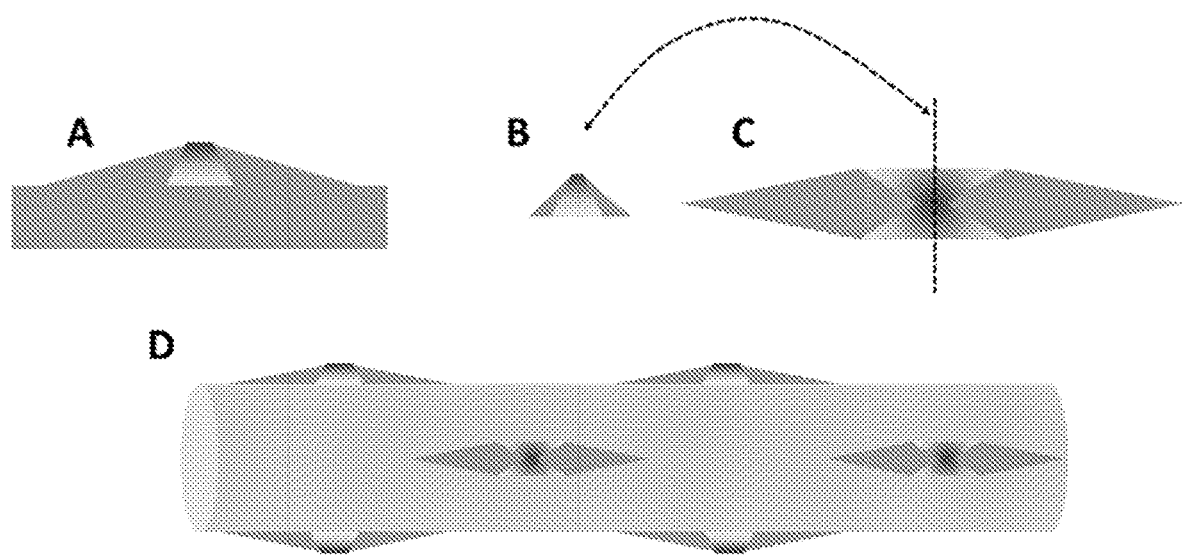

While the electrical contacts as shown in FIG. 1B-1D are conical or triangular in shape, those of skill in the art will appreciate that any shape which allows for increased charge density will be useful in the microelectrode of the present invention.

No matter the orientation of the electrodes or electrical contacts in the sidewall of the microelectrode, the electrode is embedded in a porous material that is wetted with a liquid conductor. Such liquid conductors are known to those of skill in the art, and need only be a liquid that is biocompatible and capable of allowing migration and accumulation of an electrical charge at the tip of the electrical contact. For example, and without limitation, such liquid conductors can include biologically compatible solutions containing ions, saline, artificial cerebrospinal fluid, and the like known to those of skill in the art. Similarly, the porous material can be that known to those of skill in the art, for example, and without limitation, cotton fibers, sponge glass materials, ceramics, gels, plastics, or collodion. The electrical contact(s) are arranged in the sidewall of the microelectrode and the porous material to allow for a substantially or completely flush surface with the sidewall of the microelectrode, minimizing the risk of tissue damage.

In another aspect of the present invention, electrical contacts are embedded in a non-conductive or insulating material that slopes radially outward to form outwardly-extending protrusions on the sidewall of the microelectrode, for example as shown in FIG. 1D. As shown therein, the microelectrode electrical contact can maintain a roughly conical shape as seen in a section through the long axis (FIG. 1D, panel A) and in cross-section (FIG. 1D, panel B). A top down view is shown in FIG. 1D, panel C. Also shown in panel C is the section (hatched line) representing the cross-section shown in panel B. As can be appreciated, there is a sloping rise of insulating material up to the tip of the electrical contact in the long axis of the electrode. This sloping rise, which can reach a radial distance from the perimeter of the sidewall of the microelectrode of between about 1 and about 20 microns, may minimize local microtrauma that renders recordings of extracellular action potentials less efficient. As can be seen in the top-down view (FIG. 1D, panel C) the roughly conical shape is maintained allowing for both high charge densities at the tip and sufficient surface area and thus relatively low impedances optimal for microelectrode recording of extracellular action potentials. FIG. 1D, panel D shows a possible arrangement of electrical contacts along the long axis of a microelectrode according to one aspect of the present invention. Notably, the sloping rise of the insulating material need only be arranged along the long axis of the microelectrode, such that when the electrode is inserted or withdrawn from the body, tissue is gently parted and traversed by the microelectrode. However, such gentle sloping need not be included along an axis orthogonal to the long axis of the microelectrode, as the electrode will not be moved along such an axis.

In an aspect including the sloping non-conductive or insulating material, the wetted porous material can be utilized or omitted.

A microelectrode described herein is in communication with one or more processors, to allow for a relay of information concerning extracellular action potentials and/or detection of hemoglobin and/or iron between the electrode and the one or more processors. The one or more processors can be included in one or more computing systems.

This computing system may include, but is not limited to, at least one computer having certain components for appropriate operation, execution of code, and creation and communication of data. For example, the computer includes a processing unit (typically referred to as a central processing unit or CPU) that serves to execute computer-based instructions received in the appropriate data form and format. Further, this processing unit may be in the form of multiple processors executing code in series, in parallel, or in any other manner for appropriate implementation of the computer-based instructions.

The computer further includes a system memory with computer storage media in the form of volatile and non-volatile memory, such as ROM and RAM. A basic input/output system (BIOS), with appropriate computer-based routines, assists in transferring information between components within the computer and is normally stored in ROM. The RAM portion of the system memory typically contains data and program modules that are immediately accessible to or presently being operated on by processing unit, e.g., an operating system, application programming interfaces, application programs, program modules, program data, and other instruction-based computer-readable codes.

A user may enter commands, information, and data into the computer through certain attachable or operable input devices, such as a keyboard, a mouse, etc., via a user input interface. Of course, a variety of such input devices may be utilized, e.g., a microphone, a trackball, a joystick, a touchpad, a touch-screen, a scanner, etc., including any arrangement that facilitates the input of data, and information to the computer from an outside source. As discussed, these and other input devices are often connected to the processing unit through the user input interface coupled to the system bus, but may be connected by other interface and bus structures, such as a parallel port, game port, or a universal serial bus (USB). Still further, data and information can be presented or provided to a user in an intelligible form or format through certain output devices, such as a monitor (to visually display this information and data in electronic form), a printer (to physically display this information and data in print form), a speaker (to audibly present this information and data in audible form), etc. All of these devices are in communication with the computer through an output interface coupled to a system bus. It is envisioned that any such peripheral output devices may be used to provide information and data to the user.

The computer may operate in a network environment through the use of a communications device, which is integral to the computer or remote therefrom. This communications device is operable by and in communication with the other components of the computer through a communications interface. Using such an arrangement, the computer may connect with or otherwise communicate with one or more remote computers, such as a remote computer, which may be a personal computer, a server, a router, a network personal computer, a peer device, or other common network nodes, and typically includes many or all of the components described above in connection with the computer. Using appropriate communication devices, e.g., a modem, a network interface or adapter, etc., the computer may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers may be used.

As used herein, the computer includes or is operable to execute appropriate custom-designed or conventional software to perform and implement the processing steps of the method and system of the present invention, thereby forming a specialized and particular computing system. Accordingly, the presently-invented method and system may include one or more computers or similar computing devices having a computer-readable storage medium capable of storing computer-readable program code or instructions that causes the processing unit to execute, configure, or otherwise implement the methods, processes, and transformational data manipulations discussed hereinafter in connection with the present invention. Still further, the computer may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant art(s) that the system may utilize databases physically located on one or more computers which may or may not be the same as their respective servers. For example, programming software on a computer can control a database physically stored on a separate processor of the network or otherwise.

As described above, a microelectrode described herein can be a component of a system, and can be in communication with one or more processors. As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11 and other radio frequency-based protocols and methods), analog transmissions, Global System for Mobile Communications (GSM), and/or the like.

The above computing systems can include software for targeting based on information received from the microelectrode described herein. Accordingly, provided herein are methods of targeting a microelectrode.

According to one embodiment, a method of targeting a microelectrode includes methods of characterizing neuronal spike trains detected using a microelectrode, for example a microelectrode as described herein.

Typically, microelectrode recordings of trains of extracellular action potentials (ECAPs) are obtained and analyzed in order to determine the anatomical-physiological location of the target. In addition to neuronal discharge frequencies and the relative number of neurons recorded at a specific site, the pattern of neuronal activities also provides important information. Typically the patterns are determined by visual qualitative assessment. Patterns include but are not limited to bursting, irregular, regular, and high frequency pausing. The method described herein automates the characterization of the neuronal spike train using circular statistics. These procedures can be performed any number of times for segments of any length.

Figure 2:
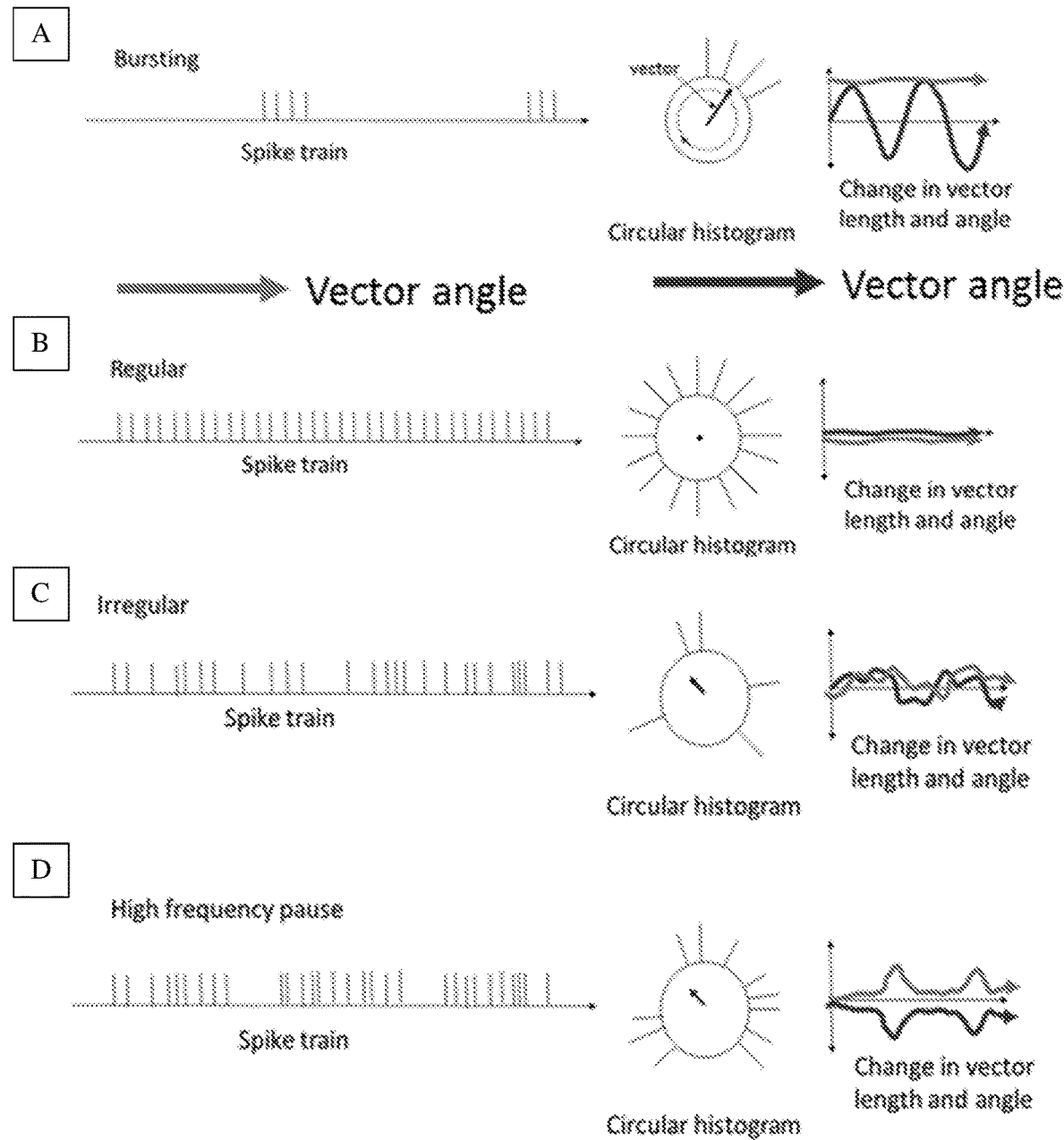
FIG. 2 shows a schematic representation of a method of guiding a microelectrode according to one aspect of the present invention. Several hypothetical examples of various neuronal spike train patterns are shown. The circular statistic is formed by taking a length of the spike train and closing it into a unit circle. The spikes associated with each extracellular action potential are plotted as vectors on the unit circle. A resultant vector of length r and angle θ are calculated. The variation in r and θ over time as a window slides through the spike train is shown for each spike train pattern.

With reference to FIG. 2, in one embodiment, to apply the targeting method, a segment of data from a recording of extracellular action potentials (ECAPs) (shown in the left column of FIG. 2), such as from a moving window, is extracted and closed upon itself to create a unit circle (shown in the middle column of FIG. 2). The relative sequential positions of the ECAPs from the segment of data forms unit vectors along the circumference (rays emanating from the closed circle in the middle column of FIG. 2). The resultant vector (center of circles in middle column of FIG. 2) is calculated from the unit vectors on the circumference representing the neuronal spikes in the segment of data. The resultant vector has a calculated length (r) and direction angle (θ). As the moving window of a specified length is moved through the recordings of ECAPs, the resultant vector length, r, and angle, θ, will change in a manner that characterizes the pattern of ECAPs.

As seen in FIG. 2, panel A, the bursting pattern of neuronal spike trains of ECAPs, will have a change over time in the resultant vector angle, θ, while the length, r, remains constant. Bursting is characterized by a short burst of neuronal ECAPs followed by silent periods. During the silent period, the r=0 and θ=0. As the window moves to include the burst, there is a rapid increase in r and θ takes on a non-zero value. The burst of neuronal activity is followed by another relatively silent period. Consequently, r remains constant. As the burst moves through the window, there is a precession of θ in a sinusoidal fashion.

With regular continuous neuronal activity (FIG. 2, panel B), the unit vectors are uniformly distributed around the unit circle. Consequently, r and θ will remain near zero as the window moves along the neuronal spike train. With irregular continuous neuronal activity (FIG. 2, panel C) r≠0, and will vary randomly but over a small range and θ≠0, and will vary randomly. Irregular high frequency pausing pattern (FIG. 2, panel D) will appear similar to the continuous irregular pattern with r≠0, varying randomly over a small range, and θ≠0 except when the pause enters the window. At that point there will be a moderate increase in r, though not as great as in the bursting pattern, and there will be a precession of θ in a sinusoidal fashion (FIG. 2, right column).

Figure 3:
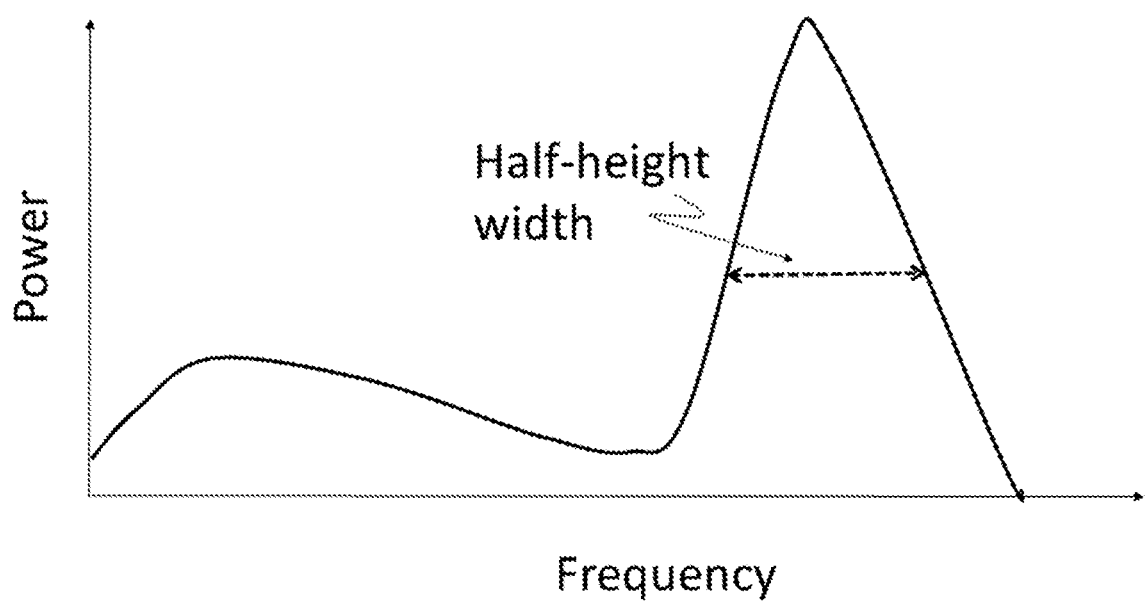
FIG. 3 shows a schematic representation of the Power Spectral Densities (PSD) of the change in the length, r, and the angle, θ, of the resultant vector over time. The half-height is the point whose power is one half of the maximum.
Figure 4A:
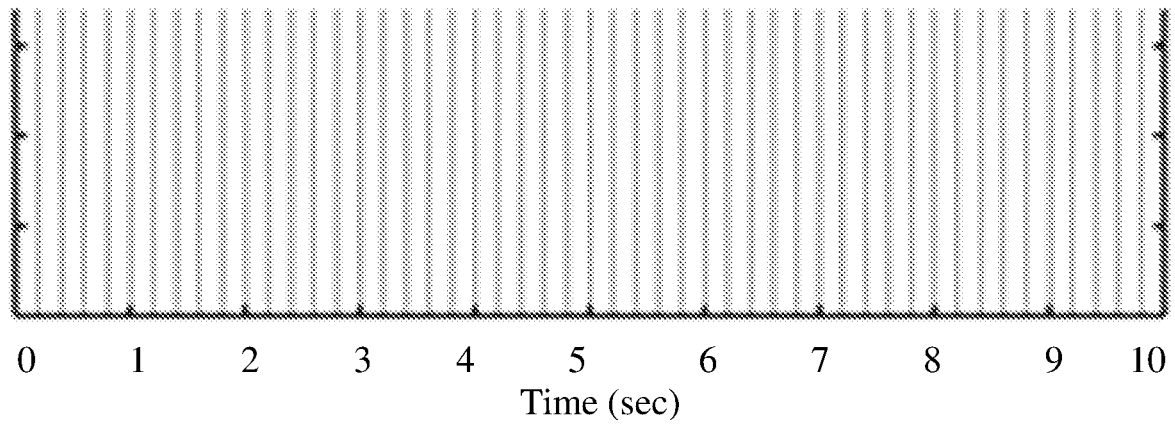
FIGS. 4A-4E show examples of simulated spike trains and an analysis method based on Brownian motion.
Figure 4A:
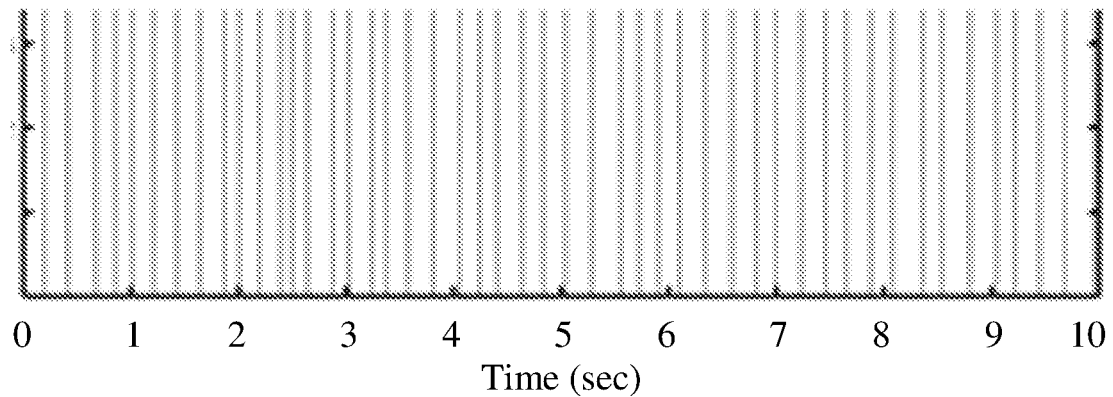
Figure 4B:
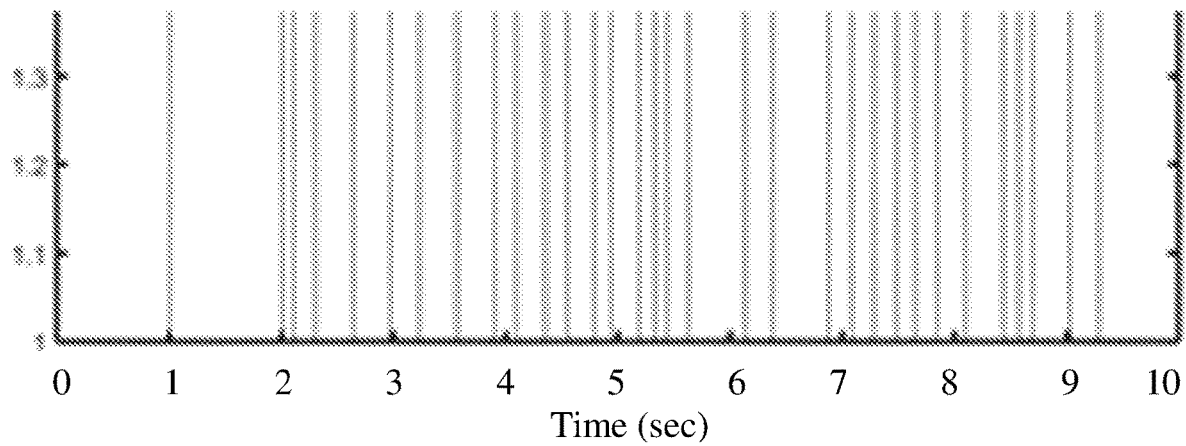
Figure 4B:
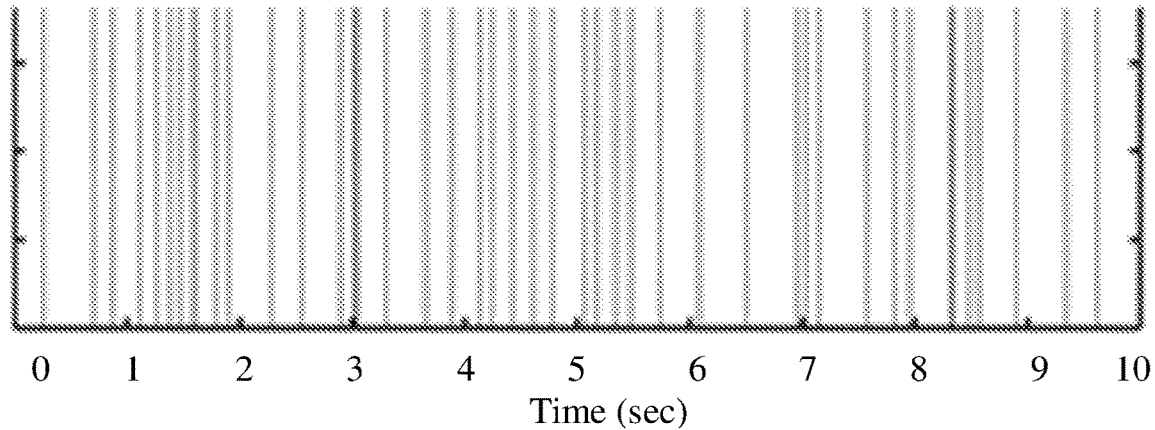
Figure 4C:
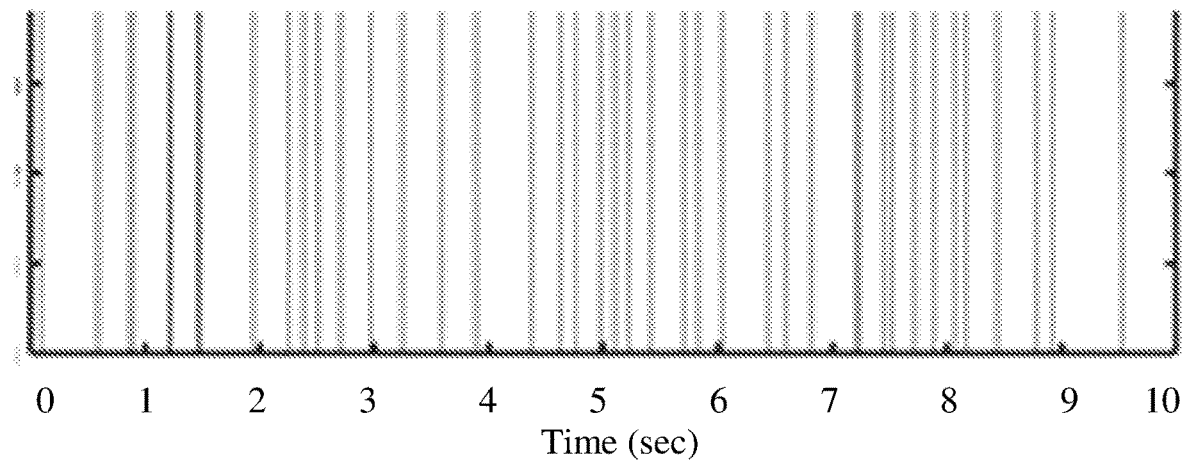
Figure 4C:
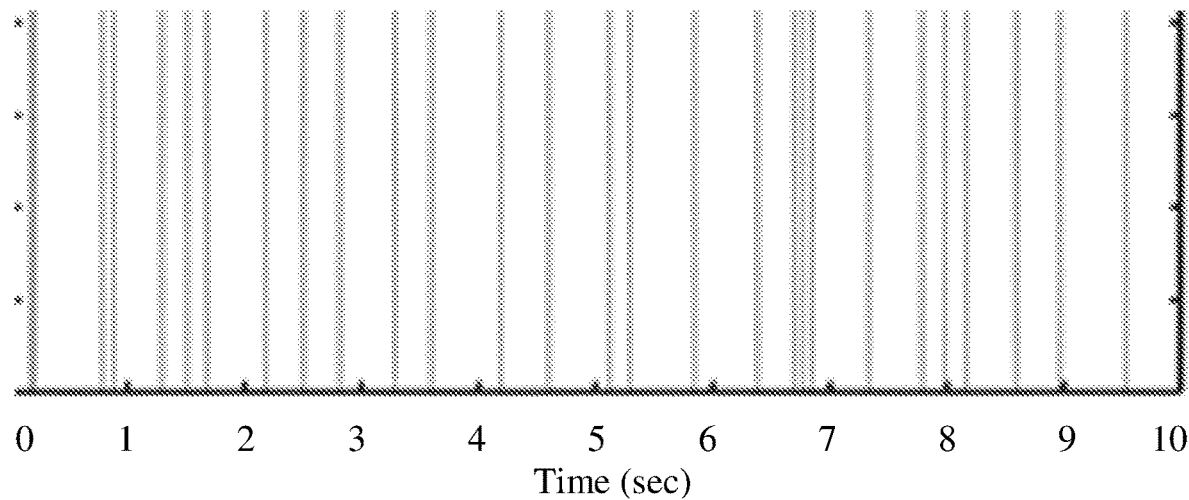
Figure 4D:
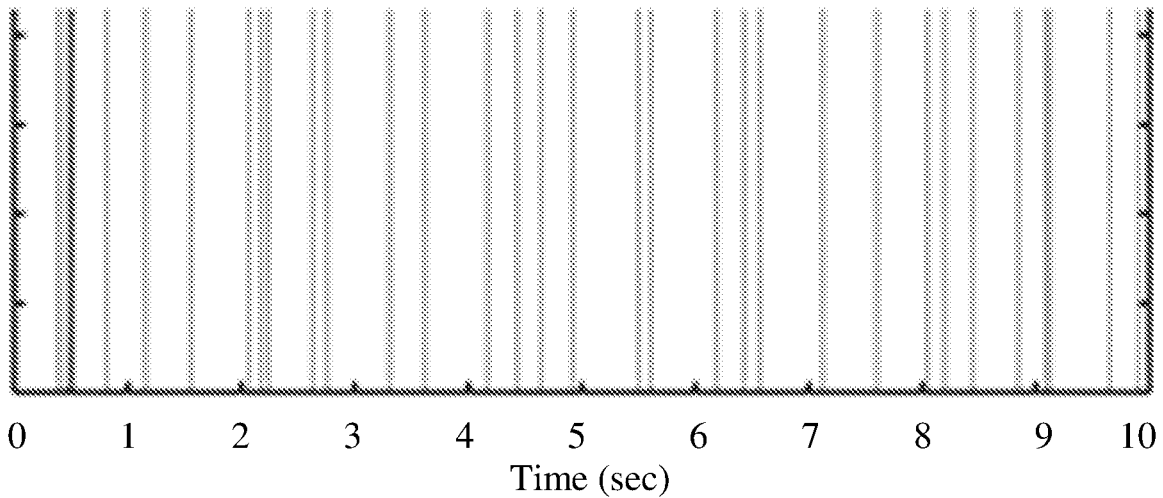
Figure 4D:
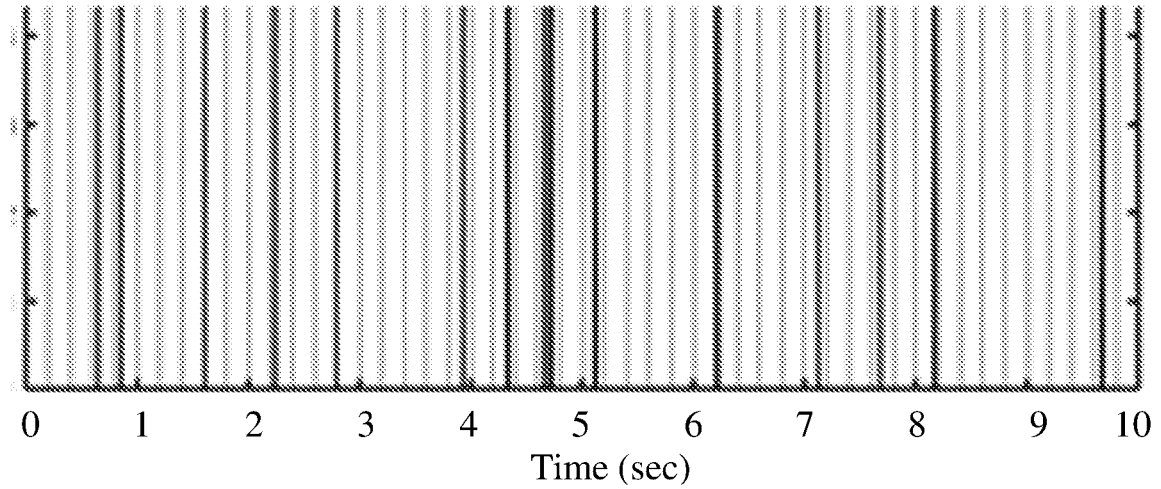
Figure 4E:
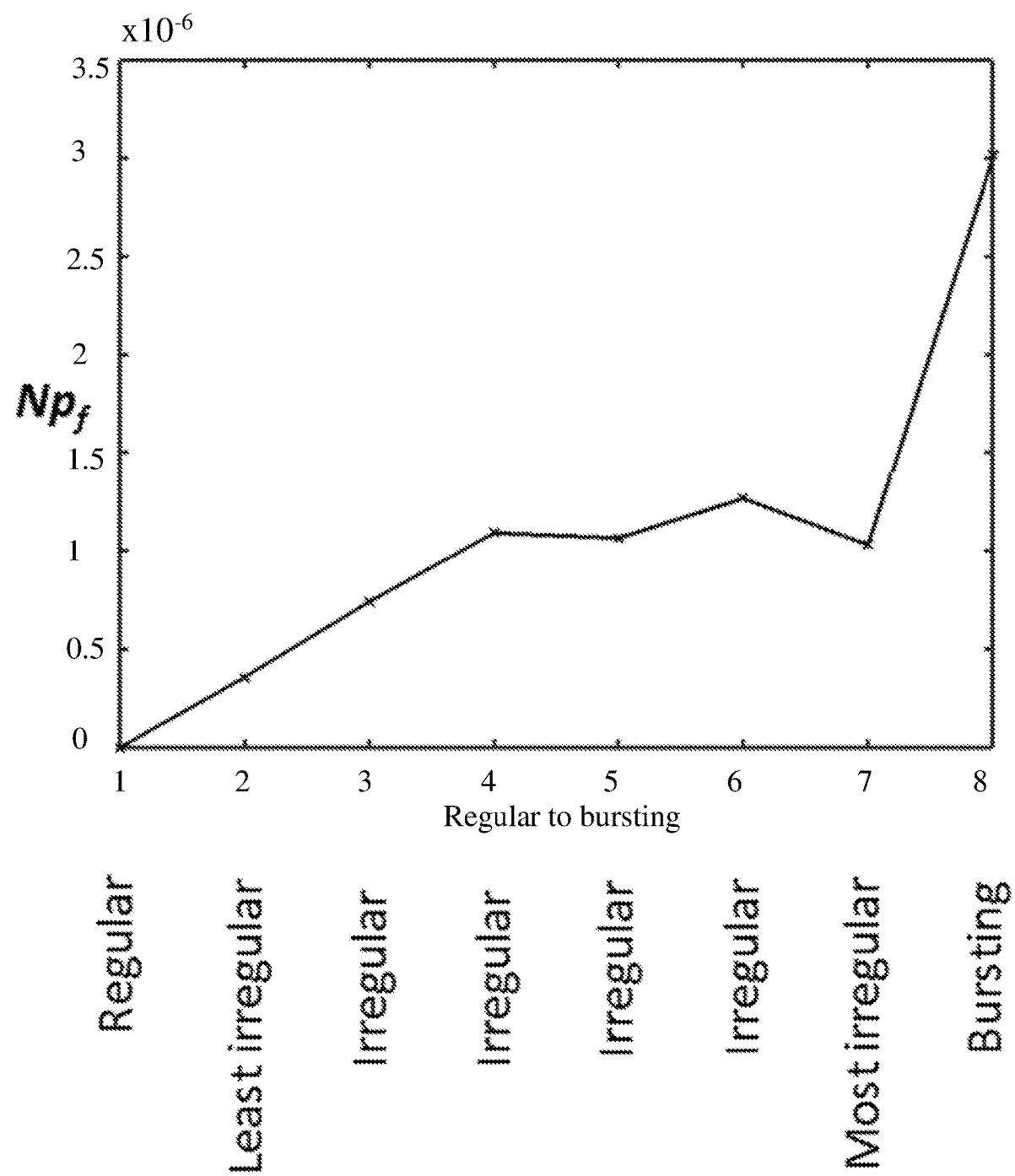

With reference to FIG. 3, shown is a representative power spectral density (PSD) of the change in the length, r, and the angle, θ, of the resultant vector over time. The PSDs are applied to the changes in r and θ over time. A peak detection algorithm is then applied to the PSD and the width of the half-heights are determined. The half-height is the point whose power is one half of the maximum. The values of the mean height of r, the widths of the half-heights of the PSD of r and the PSD of θ will indicate the neuronal spike train pattern as shown in Table 1, below.

TABLE 1

|  | bursting | regular continuous | irregular continuous | high frequency pausing |
|---|---|---|---|---|
| Vector length r PSD half-height width | wide | wide | wide | narrow |
| Mean r height | high | low | moderate | moderate |
| Vector angle θ PSD half-height width | narrow | wide | wide | narrow |

Values of various parameters associated with the length of the vector, r, and the PSDs of the variation in r and θ over time.

The values shown in the above table are descriptive; however, the present analytical method provides quantitative values. Values from actual recordings can be analyzed using multidimensional cluster analysis and the relative positions of the clusters associated with data within a database can be used to quantitate the probability that any given spike train belongs to the cluster associated with a specific pattern type using k-means analysis.

The three pattern parameters shown in Table 1 can be combined with other quantitative measures of neuronal activities at a recording site including but not limited to: 1) neuronal density (number of neurons discriminated at the recording site); 2) the total discharge frequency; and 3) duration of activity (transient versus continuous). These parameters can serve as a multidimensional space to which n-dimensional cluster analysis can be applied. Each cluster will then correspond to a specific anatomical-physiological location. For example, in the typical trajectory to the subthalamic nucleus, the thalamus, zona incerta, subthalamic nucleus and substantia nigra pars reticulate will be associated with a specific cluster in the multi-dimensional space. The values of these parameters in a specific recording site then can be translated into a probability of being associated with a specific anatomical-physiological site using k-means testing.

In addition to methods involving circular statistics, described above, methods involving analyses based on Brownian motion are disclosed herein.

Classically, an example of Brownian motion is the motion of a particle (a pollen particle) suspended in a solvent (water). The particle is seen to shake over a small spatial region. However, eventually the particle will move over a larger spatial extent and not return to the origin. This is the basis for diffusion. The rate and hence spatial extent of diffusion or movement of a particle in the solvent depends on the statistical properties of each individual movement, or "bump" between the particle and the molecules that make up the solvent. Most "bumps" are small and hence, movement will be over a very short distance. However, occasionally there will be a large "bump" that will move the particle over a very large distance. The next "bumps" likely are very small and will not bring the particle back to the original position, at least over relatively short time periods. Thus, the particle will migrate through the medium. The distance the particle moves reflects the statistical characteristic of the particle and the medium (such as the molecules of water).

The method described herein according to one aspect of the present invention take each inter-spike interval as a "bump" that moves a pointer used for analysis a distance in time, but configured as a position on a one-dimensional line. With position 0 on the time line as the initial state, each inter-spike interval will move the pointer on the time line. More exactly, the difference between each successive inter-spike interval and the mean inter-spike interval is used to move the pointer. Thus, an absolutely regular spike train where every inter-spike interval is exactly the same will keep the pointer at zero. A more irregular spike train will move the point off zero (see FIG. 4). The degree of irregularity will determine the distance the pointer is moved. Thus, the method determines the distance moved Δp as the absolute value of the difference between the mean inter-spike interval $I_m$ and the current inter-spike interval, $I_i$, where Δp=(|Im−Ii|). The final position of the pointer, pf, equals ΣΔp. In use, the position of the final pointer is normalized by dividing by N where N is the number of inter-spike intervals. The normalized pointer, $$Npf = \frac{\sum \Delta p}{N}.$$

The final position of the pointer, pf, is determined, in part, by the incidence histogram of the inter-spike intervals (probability density function). If the probability density function is Gaussian, then one might expect that pf would always return to the 0 position, based on the Functional Central Limit Theorem regardless of the spike train pattern. However, this is not the case in the method for three reasons. If the sequence of movements of the pointer is from a Markovian process, then the pointer is likely to converge back to position 0. The key is that the sampling of each inter-spike interval is a non-Markovian process that displays a dependence on the sampling history. The history is due to regression towards the mean. Thus, a subsequent inter-spike interval is most likely to be closer to the mean than the previous inter-spike interval with the probability determined by the probability density function; hence, a history dependence characteristic of a non-Markovian point process.

Another factor in the method is the use of the mean inter-spike interval which exaggerates the effects of outliers in a non-symmetric incidence interval histogram (probability density function) such as a Poison distribution which is most typical of neuronal spike trains. Thus, using the mean inter-spike interval increases the distance the pointer will move when an outlier inter-spike interval is encountered.

In addition, taking the absolute difference between the mean and sample inter-spike interval prevents the point from returning to the origin.

The three factors described above allows differentiation of a bursting or pausing irregular spike train from other types of irregular spike trains. Thus, the method will be particularly useful in characterizing microelectrode recording sites during intraoperative neurophysiological mapping for DBS lead implantation surgery. Thus, the normalized pointer final position, Npf, can be used as a single (economical) yet robust characterization of the spike train point process.

With reference to FIG. 4, shown are examples of simulated spike trains with various frequencies (regular, irregular, bursting) and a chart showing normalized pointer position (Npf) and the degree of regularity of the spike train (interspike interval). As can be seen, the greater the irregularity, the further from a point 'O' the pointer falls.

The methods described above can be used to provide more accurate identification of various phenomena in electrophysiological recordings, and removes subjective biases from the analysis. A more accurate identification improves target localization in MERs, and allows for more accurate delivery of interventions, for example, drugs, biological factors, or electrotherapy. Methods for target localization using macroelectrode recordings are provided in, for example, U.S. Patent Publication No. 2016/0051812, the contents of which are incorporated herein by reference in their entirety.

Also provided herein are additional methods for targeting, including approaches for more sensitive analyses of thresholds and filtering of noise/artifacts from sensed electrical activity.

Prior to the methods disclosed herein, in a MER containing neuronal spikes, one could apply the concept of regression towards the mean to determine the necessary threshold for differentiating signal—neuronal spikes—form noise. Typically, neuronal spikes clearly stand out from noise in two ways. First, the neuronal spikes have voltage amplitudes much higher than any voltage amplitudes in the noise. Second, and crucially, there are far fewer voltage amplitudes associated with the spikes than there are associated with the noise. This allows "daylight" between the neuronal spikes so that the spikes can be recognized. FIG. 5A, top panel shows how the concept of regression towards the mean can be used to set a threshold to detect neuronal spikes.

Specifically, FIG. 5A, top panel, shows an expanded segment of a MER showing a sequence of voltage amplitudes (represented by the small circles) in two segments of noise and in the signal, a neuronal spike. As can be seen, the amplitudes in the signal are higher than those of the noise. Because there are many more data points in the noise, the statistical distribution of the amplitudes will be dominated by the noise. Thus, the degree any data point is greater than the mean of the amplitudes, the higher is the probability that the next amplitude will be less. This is true until amplitudes are reached that are just higher than the maximum noise amplitude. In this case the next amplitude has a higher probability of being greater than the just measured amplitude because the initial voltages in the spike are in the distribution of the voltage amplitudes determined by the amplitudes within the spikes. Thus, considering any amplitude $a_i$ that is within the distribution of the noise, as $a_i$ increases the probability that $a_{i+2}$ being greater than $a_i$ becomes less. When the amplitude $a_i$ just exceeds the maximum amplitude in the noise, the probability that $a_{i+2}$ being greater than $a_i$ increases. The amplitude where $a_{i+2}$ first becomes consistently greater than $a_i$ represents the threshold for detecting neuronal spikes. The $a_{i+2}$ amplitude is used rather than the $a_{i+1}$ to avoid digitization noise where the digitized value of the amplitude toggles in the least significant bit.

Figures 1, 5B:
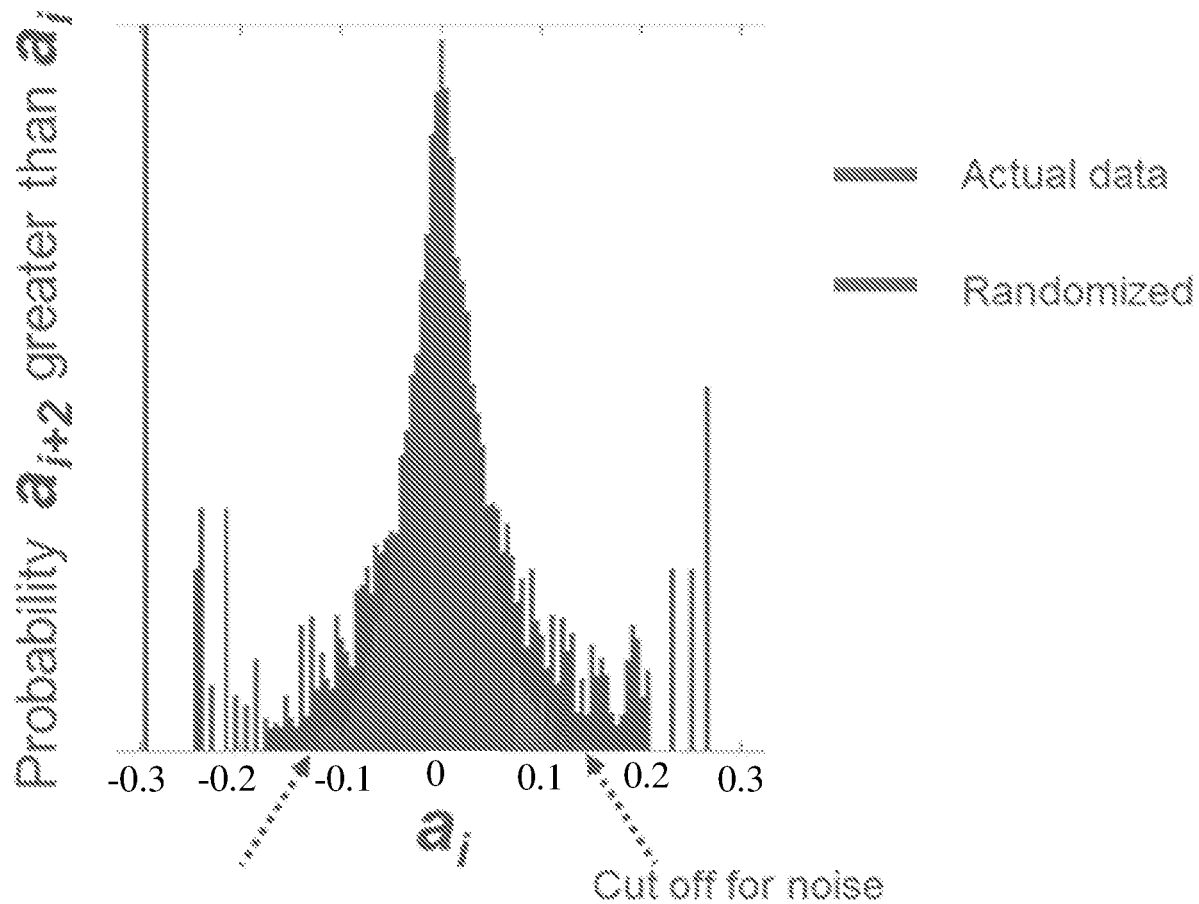
Figures 2, 5B:
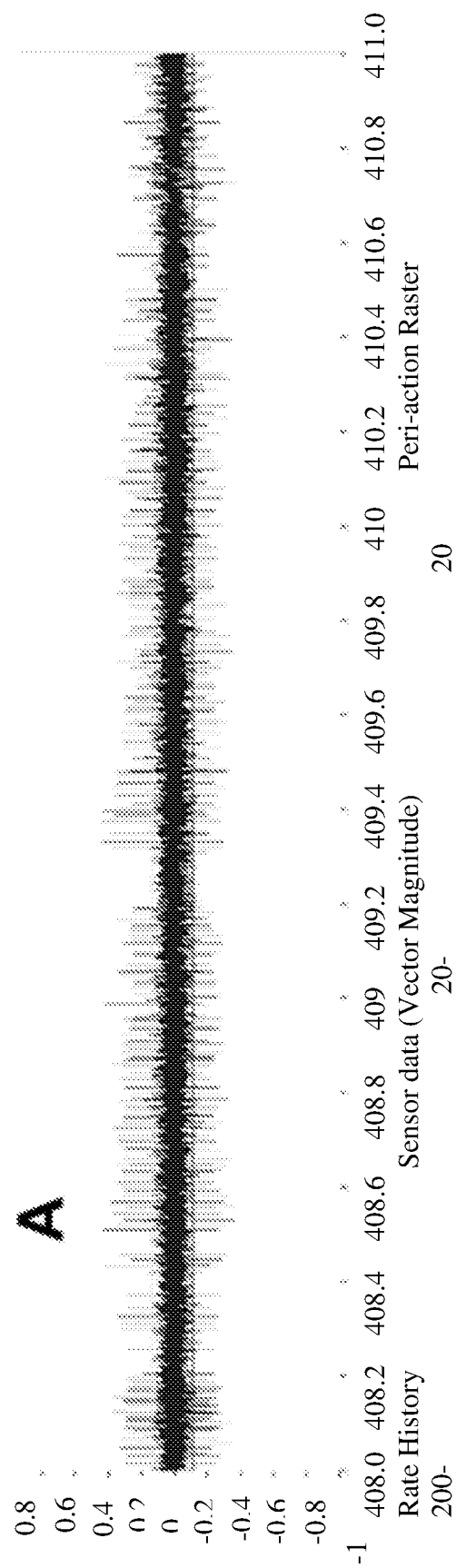
Figures 3, 5B:
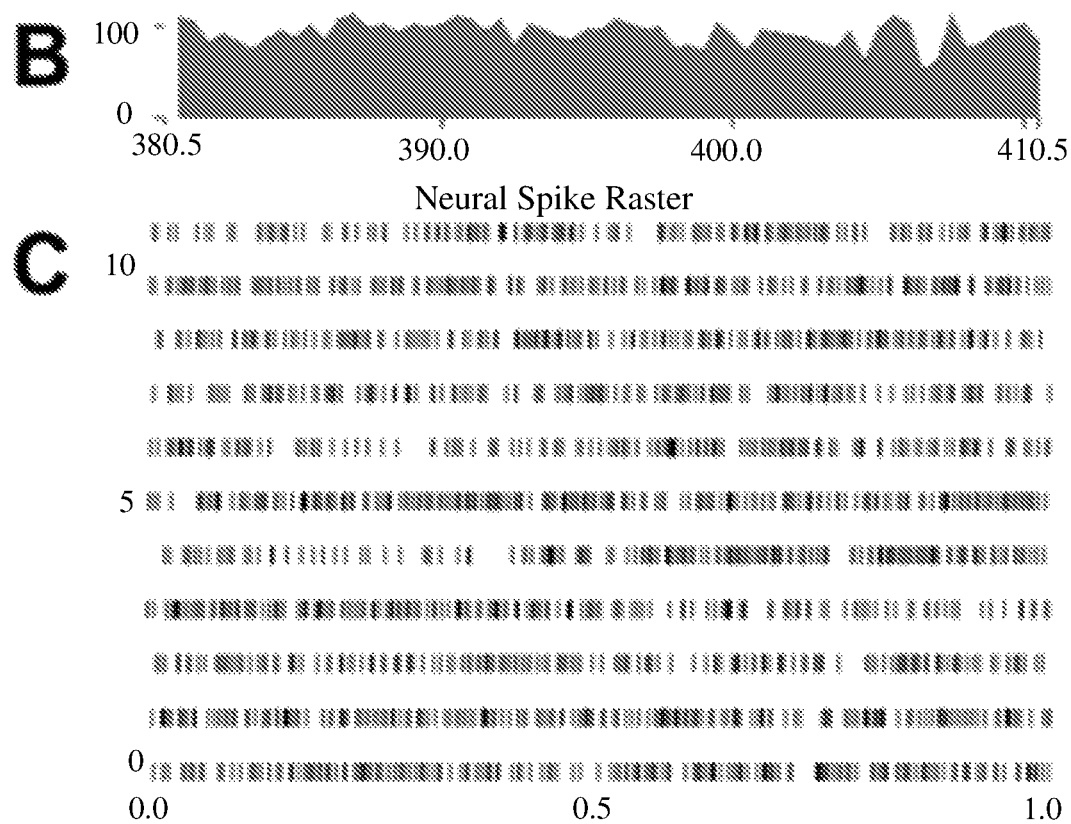

In previous methods, one could plot the incidence (the probability) where the $a_{i+2}$ amplitude is greater than $a_i$ for each value of $a_i$ (FIG. 5A, bottom panel). If one were to plot such as distribution for a MER containing neuronal spikes, a distribution similar to the blue distribution shown in FIG. 5B, top panel. As can be seen, there are three peaks in the distribution, the central peak represents the noise and the two side peaks represent the positive and negative peaks in the neuronal spikes. Next, the order of the voltage amplitudes are randomized which is analogous to having the NBA players retake random positions in the line. The red distribution in FIG. 5B, top panel shows the distribution of the probability of the $a_{i+2}$ amplitude being greater than the $a_i$ amplitude and demonstrates only a single peak consistent of the effect of noise. The difference between the red and blue distributions reflects the presence of the neuronal spikes. The threshold for detection of the neuronal spikes is where the tails of the red distribution end. The method was applied repeatedly to anticipate changes in noise levels.

Figure 6:
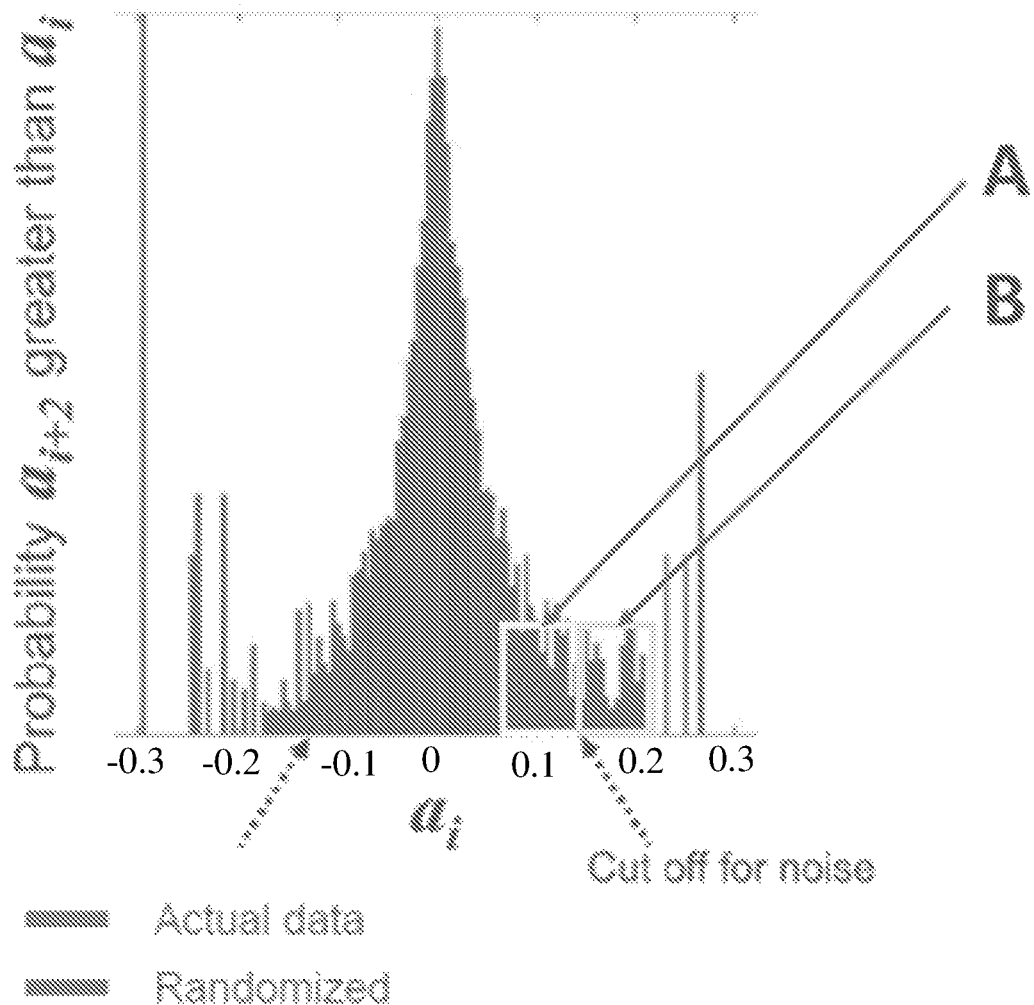
FIG. 6 shows a method of determining threshold and probability that a detected electrical signal is a neuronal spike train rather than noise or artifact according to one aspect of the present invention. As can be seen by the data contained within the green rectangle (B), there is an increasing probability function and demonstrated the increasing contribution of the amplitudes of the neuronal spikes while the negative slope of the distribution, seen in the yellow rectangle (A) represents diminishing contributions from noise. The new threshold algorithm is designed to detect the upslope in the distribution of the actual data.

However, this prior method is deficient in a number of respects. Specifically, the above, original threshold detection algorithm used the point where the distribution of the randomized data (probability that the $a_{i+2} > a_i$) no longer overlapped with the distribution of the actual data. In use, occasional MERs contained very large number of spikes such that the data from the regions of the MER represented by noise no longer were the very dominant factor in the distributions of the probabilities that $a_{i+2} > a_i$. This means that the original cutoff would either be at too high of an amplitude and thereby miss true neuronal spikes, or be too low and detect noise confused for neuronal spikes (FIG. 6). Specifically, FIG. 6 shows, data contained within the green rectangle (B), there is an increasing probability function and demonstrated increasing contribution of the amplitudes of the neuronal spikes while the negative slope of the distribution, seen in the yellow rectangle (A) represents diminishing contributions from noise. The threshold algorithm described herein instead detects the upslope in the distribution of the actual data.

Figure 7A:
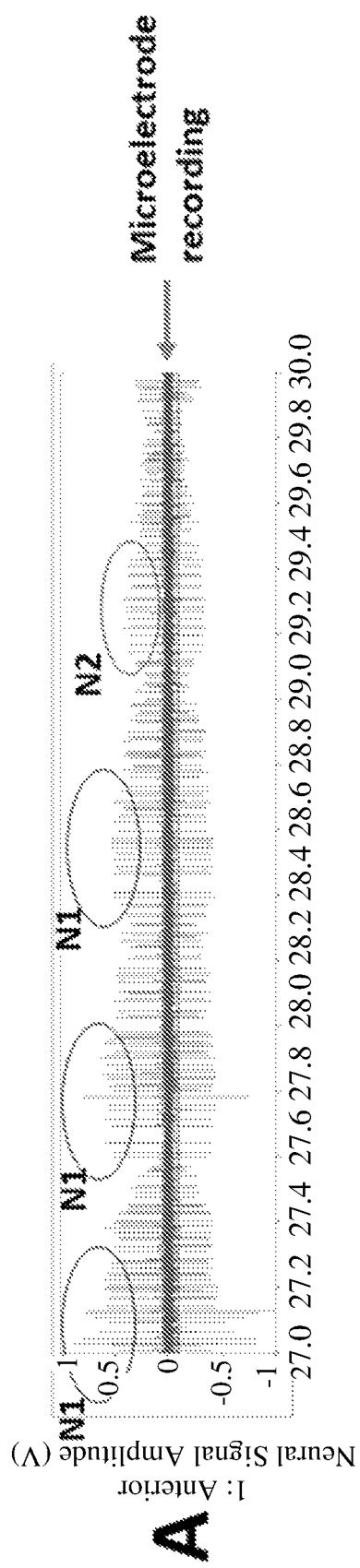
FIGS. 7A-7B show a sample of raw MER data (A) and graphs of the distributions of the probability functions as described in FIG. 10 for both the actual and the randomized data (B). As can be appreciated in A there appears to be approximately two sets of amplitudes representative of two neurons (N1 and N2) based on their positive amplitudes. These neuronal amplitudes are associated with peaks in the probability function of the actual data that is clearly different from the distribution of the randomized data. The issue becomes of detecting the upslopes in the distributions of the actual data which represents significant contributions from the amplitudes of the neuronal spikes. The approach taken is that the upslopes proceed from a local minima and the new invention is a means of detecting local minima.
Figure 7B:
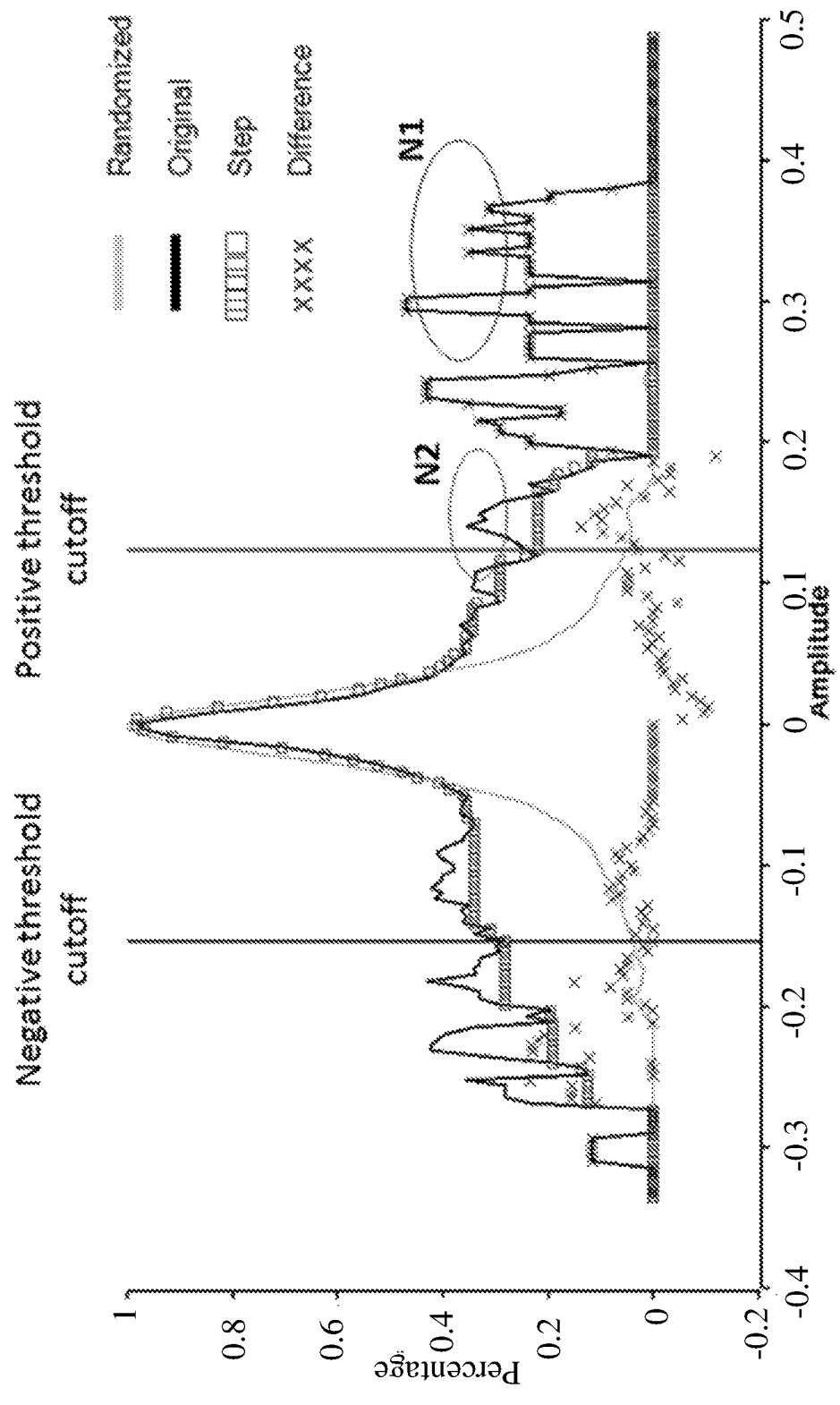

Thus, the reliable detection of the upslopes in the distributions for the actual data is required. As can be seen, the actual data within the green rectangle in FIG. 6 contains an upslope. FIG. 7 shows a sample of raw MER data (panel A) and graphs of the distributions of the probability functions as described in FIG. 6 for both the actual and the randomized data (panel B). As can be appreciated in panel A there appears to be approximately two sets of amplitudes representative of two neurons (N1 and N2) based on their positive amplitudes. These neuronal amplitudes are associated with peaks in the probability function of the actual data that is clearly different from the distribution of the randomized data.

As can be seen from the raw MER (FIG. 7, panel A), there appears to be two different sets of neuronal spikes based on their positive amplitudes (N1 and N2). The distribution of the probabilities $a_{i+2} > a_i$ with increase value of $a_i$ is shown by the black line in FIG. 7, panel B. As can be seen, the central and highest peak in the distribution is at $a_i=0$ which corresponds to the dominance of the noise. Moving in the increasingly positive direction (rightward) shows a series of peaks roughly corresponding to the different neuronal spike amplitudes seen in the raw MER (FIG. 7, panel A). The number of peaks is unimportant for the purposes of establishing a threshold for the detection of neuronal spikes. The function of determining the number of different neurons represented in the MER is discussed below.

The issue becomes reliable, accurate detection of the upslopes in the distributions of the actual data which represents significant contributions from the amplitudes of the neuronal spikes. The approach described herein is that the upslopes proceed from a local minima and the method described herein provides a reliable means for detecting the local minima.

Figure 8:
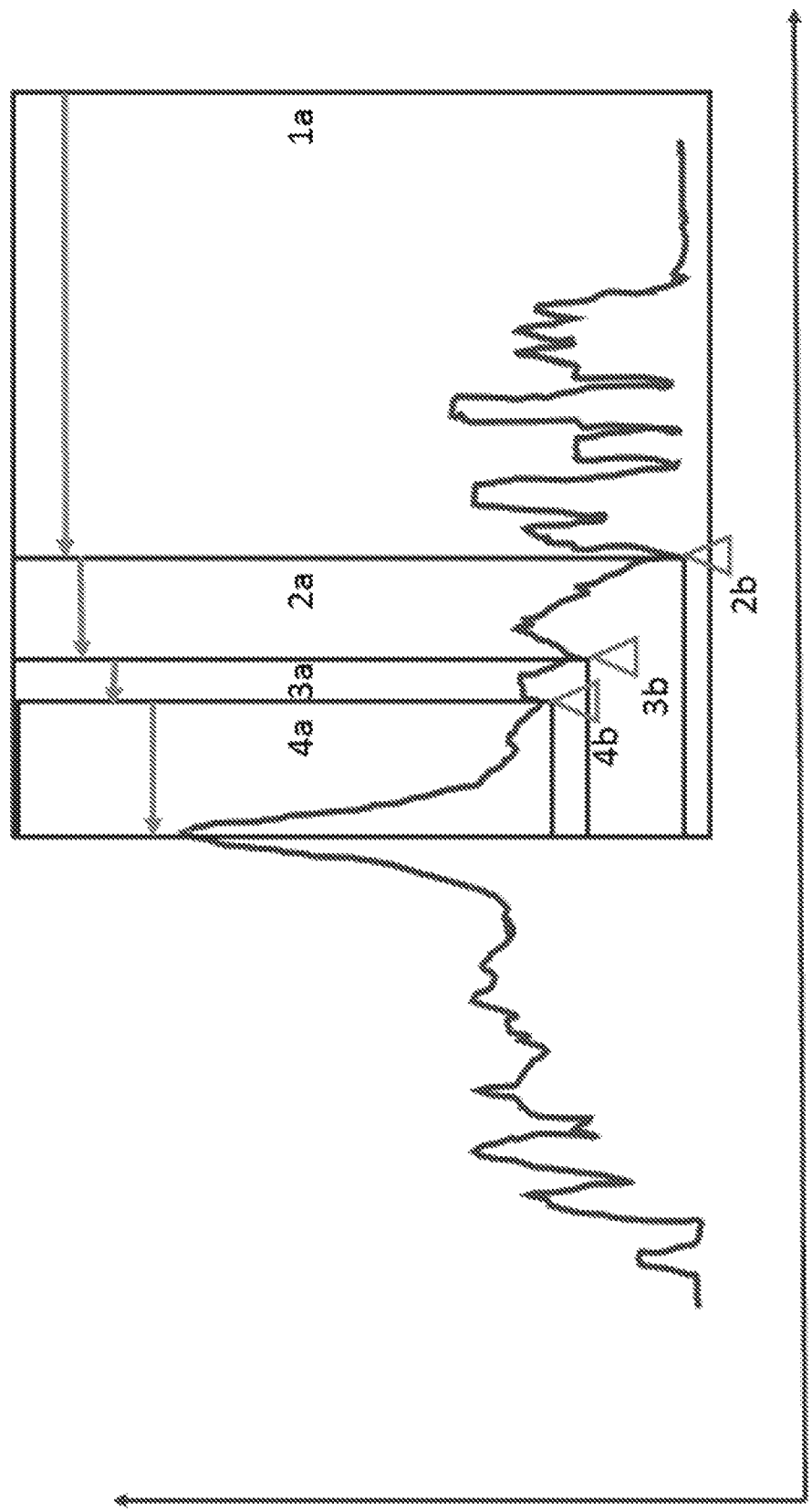
FIG. 8 shows a method for detecting local minima in the distribution of the probabilities in the actual data (represented by the blue line) starts from creating a window, in this case, beginning at amplitude=0 and extending in a positive direction (rightward) to the end of the distribution (1a). The minimum value in the window is determined (2b). The window is progressively narrowed and the minimum value repeatedly determined. For example, when the window is reduced to 2a, there is a new minimum. The point just prior to the new minimum represents the first local minima. The window continues to be progressively narrowed until a new minimum value is found, for example 3a. Again, the positive extent of the window just before the change in the minimum value is taken as another local minima (3b). The process continues, for example window 4a, until the next local minimum equals the value of the probabilities at the central peak. The amplitude of the local minima just prior to reaching the central peak is taken as the threshold for detecting neuronal spikes above the noise.
Figure 9A:
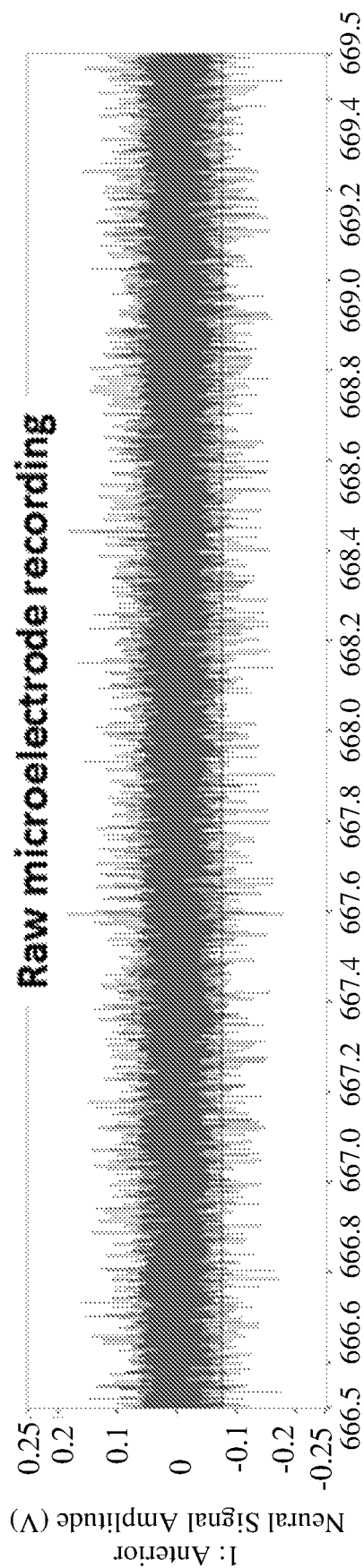
FIGS. 9A-9B show an example of analyses with a spike filter according to one aspect of the present invention disengaged. The raw MER signal is shown to have a great deal of spike-like discharges and indeed it is difficult to differentiate artifact versus neuronal spikes. Both the artifact and neuronal spikes cross the thresholds and are shown in the wrapping raster where each tic represents the time a spike exceeded the thresholds. The rows represent a continuous spike train. Also shown are two indicators, A, which reflects the amount of MER signal above outside the threshold indicating spikes (both artifact and neuronal). Indicator B shows the number of spikes that pass through the spike filter to indicate the presence of neuronal spikes in the MER despite the micro-drive artifact.
Figure 9A:
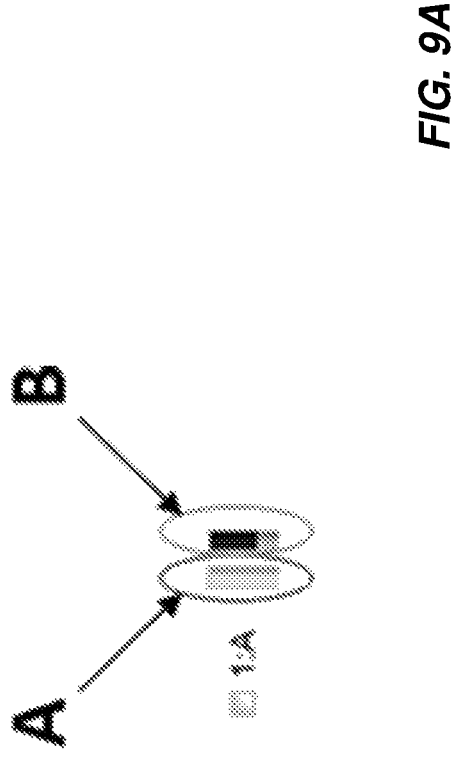
Figure 9B:
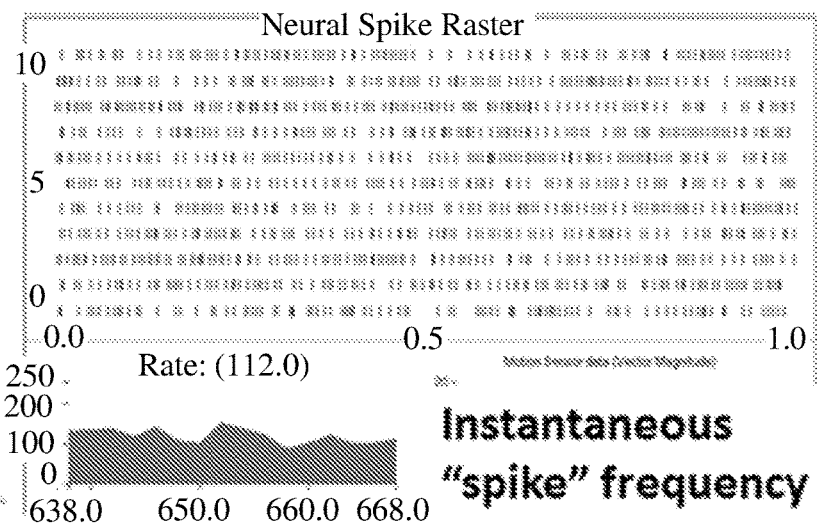
Figure 9B:
Figure 9B:
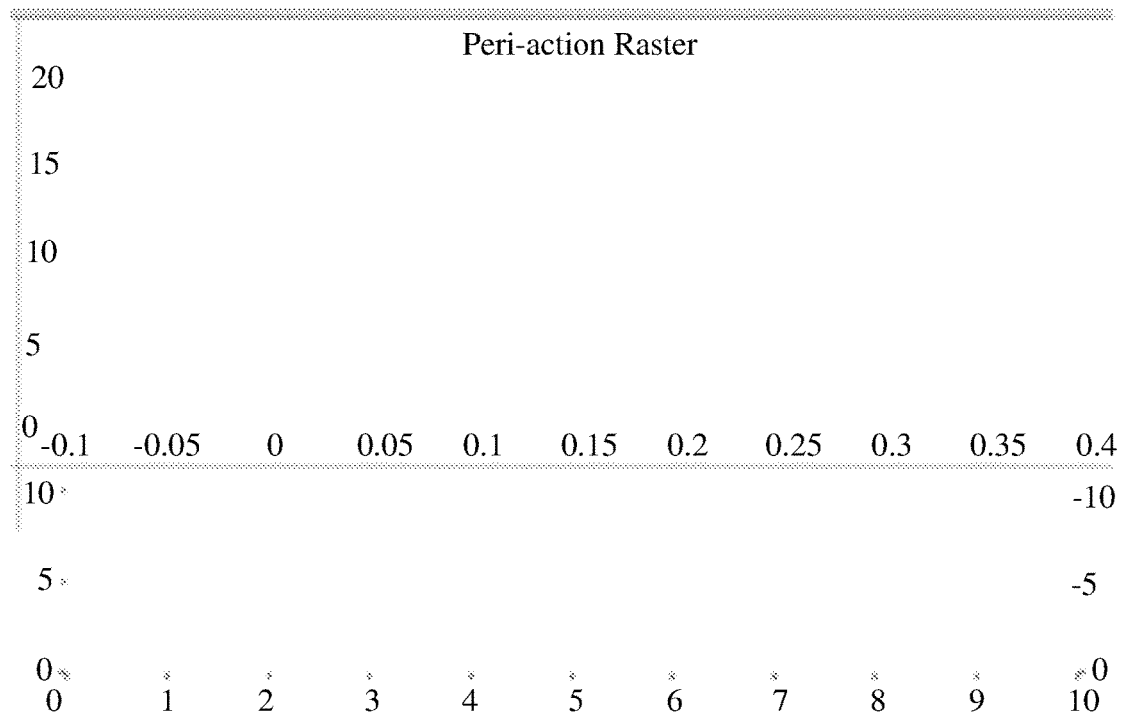

The method begins by taking the largest window containing the data for which the local minima is to be determined (FIG. 8). In the method, the minimum value within the window of data is determined. The window is progressively narrowed and the minimum value repeatedly determined. The first time that the minimum value increases represents movement of the window just beyond the deepest local minima. The process is repeated identifying each new local minima until the window has shortened to the central peak. The graph of the local minima as the window is progressively narrowed is shown by the line labeled Step. The next step is to subtract the Step function from the distribution of the actual data. The difference reflects the contribution of the amplitudes within the spike versus the noise. The resulting function labeled Difference provides an estimate of the contributions of the amplitudes associated with neuronal spikes. When the amplitude of the Difference first rises above a user determined threshold, proceeding outward from amplitude=0, the threshold for neuronal spike detection is set.

With reference to the specific example in FIG. 8, detecting local minima in the distribution of the probabilities in the actual data (represented by the blue line) starts from creating a window, in this case, beginning at amplitude=0 and extending in a positive direction (rightward) to the end of the distribution (1a). The minimum value in the window is determined (2b). The window is progressively narrowed and the minimum value repeatedly determined. For example, when the window is reduced to 2a, there is a new minimum. The point just prior to the new minimum represents the first local minima. The window continues to be progressively narrowed until a new minimum value is found, for example 3a. Again, the positive extent of the window just before the change in the minimum value is taken as another local minima (3b). The process continues, for example window 4a, until the next local minimum equals the value of the probabilities at the central peak. The amplitude of the local minima just prior to reaching the central peak is taken as the threshold for detecting neuronal spikes above the noise.

Also provided herein, in addition and complementary to threshold detection as described above, is a filter for noise and artifact present in electrophysiological recordings.

Current systems and methods include robust algorithms to determine whether spikes are contained within an MER and automatically extract and characterize those spikes even in the face of electrical noise. This is possible because the noise dominates the statistical distribution of electrical amplitudes in the MER. However, artifact is more difficult because of its intermittent or spike-like features. Consequently, there has not been any effective way of automating differentiation of artifact from neuronal spikes. Until now, the distinction required the subjective judgment of highly trained and experienced intraoperative neurophysiologists. The subjective nature of such analyses is not desirable.

A particularly limiting artifact for electrophysiology is that associated with micro-drives needed to advance the microelectrode through the brain. Often, it simply is not possible to look for spikes in the presence of artifact as the micro-drive advances. The presence of micro-drive artifact requires the operator to advance the micro-drive in very small steps, pausing between each step to check if neuronal spikes are present. This is highly inefficient and greatly increases the time and expense of DBS lead implantation surgery.

To this end, the filter described herein is designed to extract neuronal spikes even in the presence of artifact, such as micro-drive artifact. Thus, the user can continuously advance the microelectrode until the filter determines that neuronal spikes are in the MER, even in the presence of marked artifact. Thus, the user can "record-on-the-fly," greatly increasing the efficiency of MER thereby reducing time and cost.

FIG. 9 shows a simulated MER containing both micro-drive artifact and neuronal spikes without any filtering. As can be appreciated, the micro-drive artifact looks very similar to the neuronal spikes. Indeed, even very experienced intraoperative neurophysiologists would find it difficult to know with confidence whether the MER contains neuronal spikes as well as the micro-drive artifact. In FIG. 9, two indicators are shown. Indicator A, which reflects the amount of MER signal above the threshold indicating spikes (both artifact and neuronal), and indicator B, which shows the number of spikes that pass through the filter to indicate the presence of neuronal spikes in the MER despite the micro-drive artifact. Because of the spike-like features of the micro-drive artifact and the relatively large amplitudes comparable to actual neuronal spikes, the algorithms to set amplitude thresholds for detection of spikes cannot differentiate micro-drive artifact spikes from neuronal spikes and consequently both are included in the wrapping raster of neuronal spikes.

Figure 10:
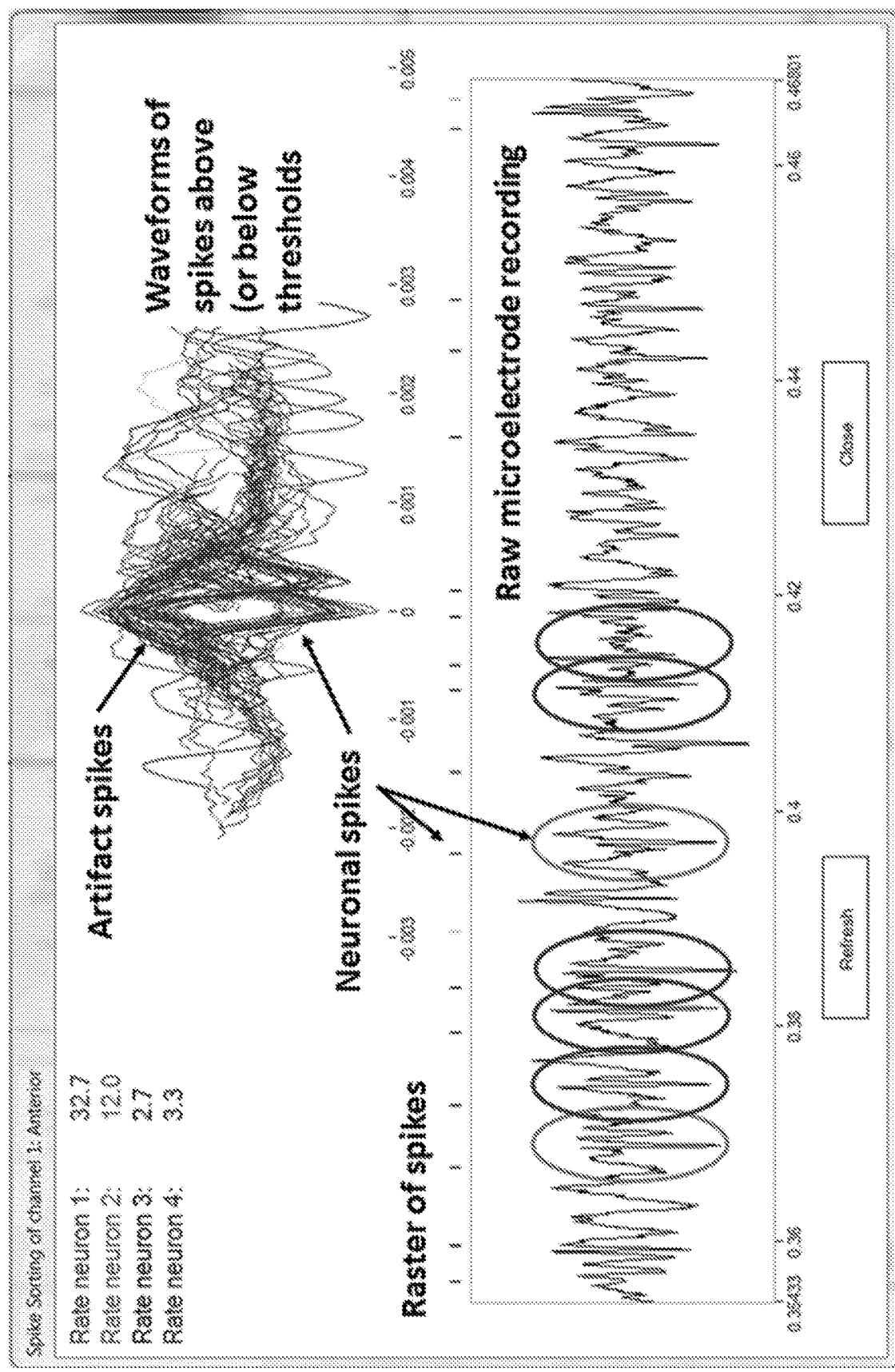
FIG. 10 shows analyses of a spike hunter function with the spike filter disengaged. This function discriminates spikes that exceed thresholds, characterizes the waveform of each spike and then classifies the spikes base on a 6-dimensional cluster analysis. As can be seen, the red waveforms are artifact spikes. The half-height width greatly exceed those of the neurons (identified by the green and blue waveforms. The raster comprises a sequence of colored tic marks, each color linked to a specific spike. As can be seen, both artifact and neuronal spikes are discernable in the expanded view of the MER.

In FIG. 10, a segment of MER data is shown (such as that shown in FIG. 9). In accordance with the present method, extracted spikes with amplitudes greater than the thresholds determined from the noise also in the MER data are shown. As can be seen, artifact has been included in the spikes detected in addition to the presence of true neuronal spikes. In FIG. 10, the method discriminates spikes that exceed thresholds, characterizes the waveform of each spike and then classifies the spikes base on a 6-dimensional cluster analysis. As can be seen, the red waveforms are artifact spikes. The half-height width greatly exceed those of the neurons (identified by the green and blue waveforms. The raster comprises a sequence of colored tic marks, each color linked to a specific spike. As can be seen, both artifact and neuronal spikes are discernable in the expanded view of the MER.

Figure 11A:
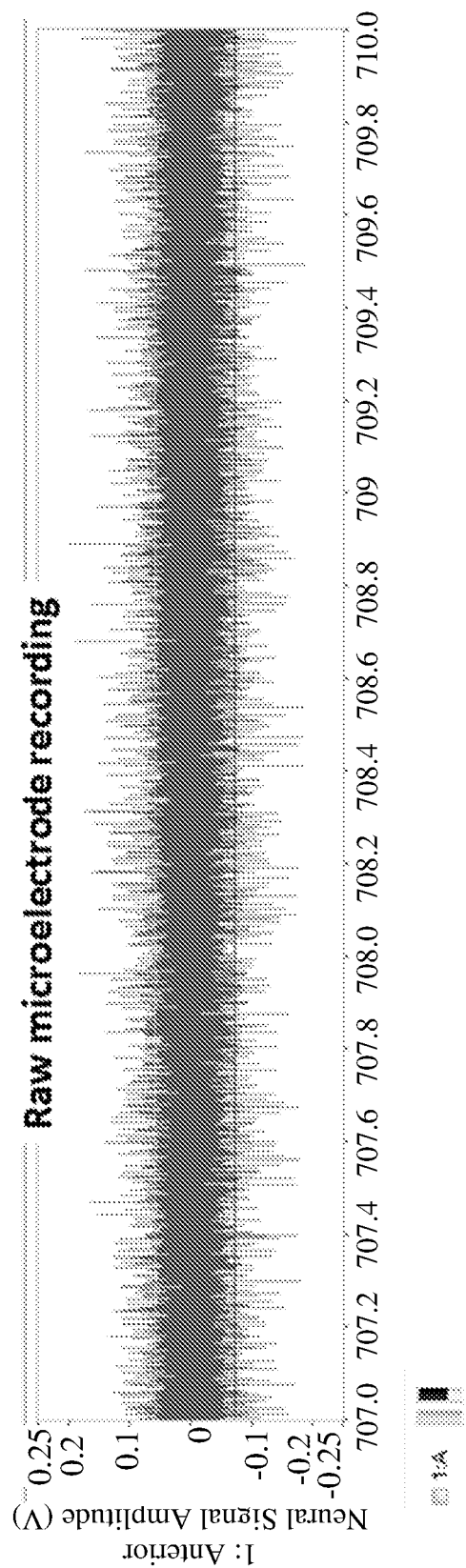
FIGS. 11A-11B show output of the analyses for the same MER shown above, with a spike filter engaged. As can be seen, the raw MER is the same as that shown in FIG. 9. The wrapping raster demonstrates that artifact spikes are no longer counted when the spike filter is engaged. The raster now contains only neuronal spikes.
Figure 11B:
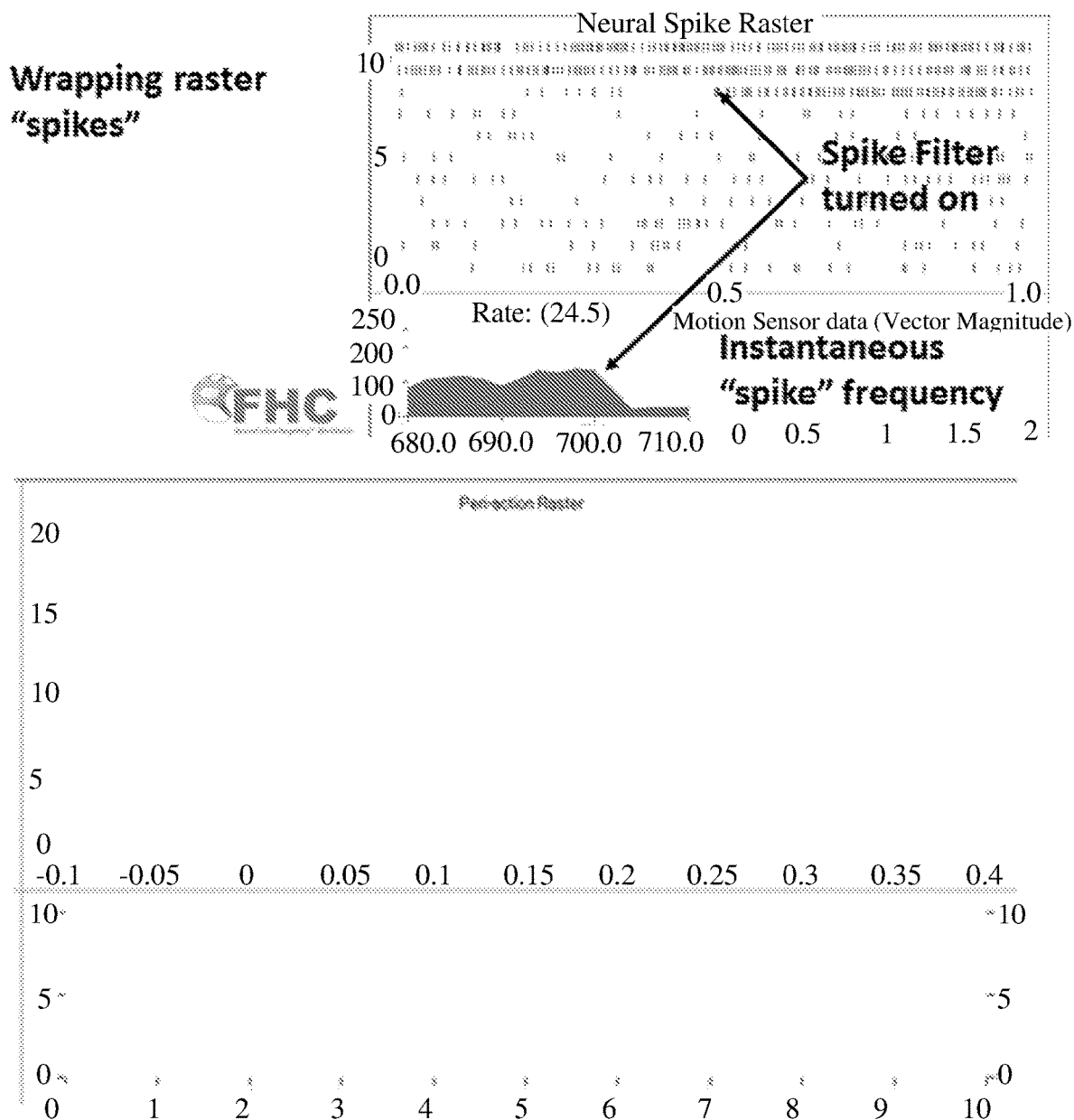

FIG. 11 shows the analyses of the same data shown in FIG. 10 except that the filter has been engaged. As can be seen, the raw MER is identical to that shown in FIG. 10 when the filter is disengaged. However, the wrapping raster no longer includes "spikes" due to artifact and leaves behind only neuronal spikes.

Figure 12:
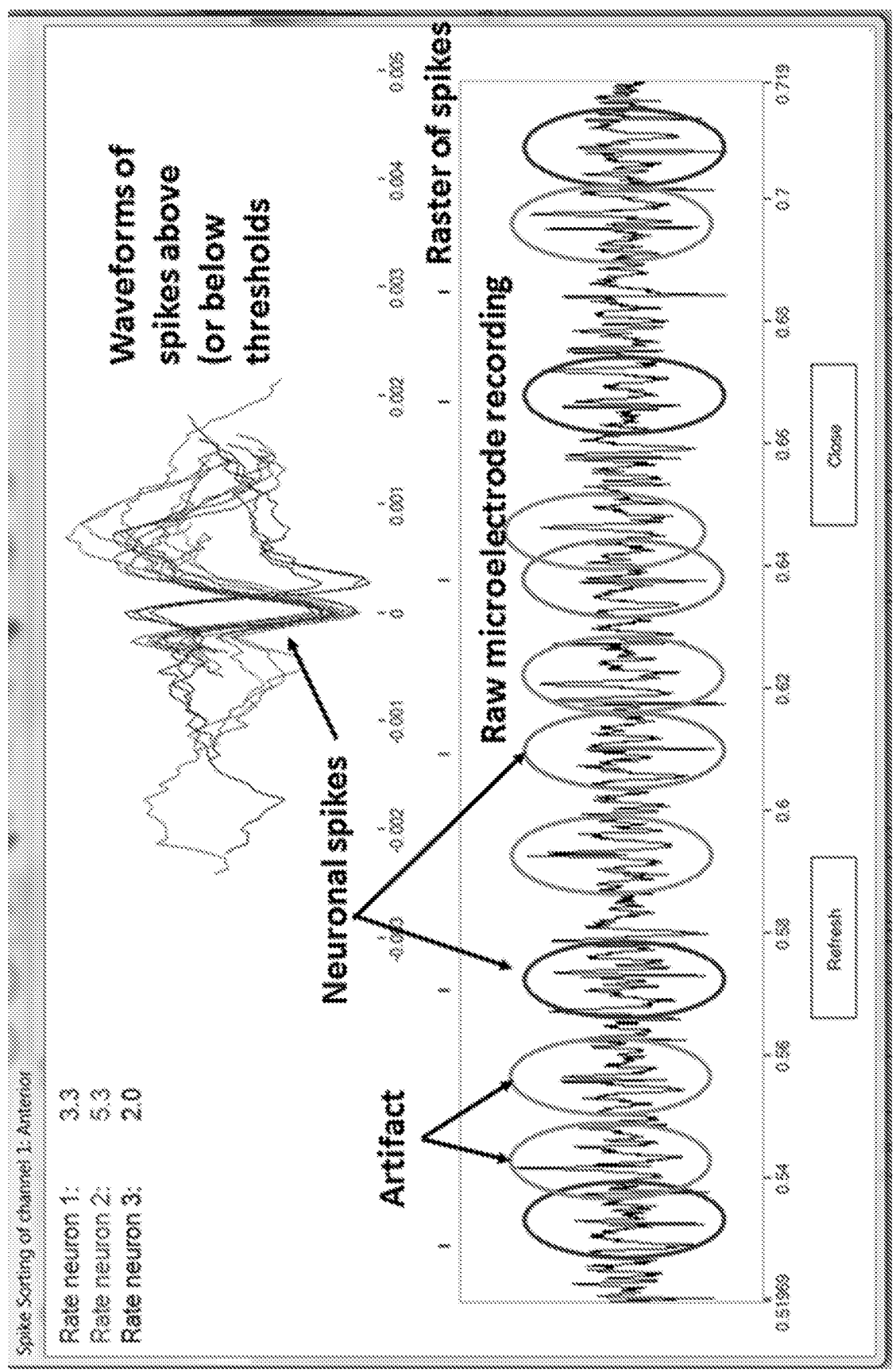
FIG. 12 shows results from a neuron hunter function with the spike filter engaged from the MER signals shown in FIGS. 8 and 10. As can be seen, the waveforms of spikes passed through by the Spike Filter are very likely to be actual neuronal spikes. Note in the expanded MER sample, the artifact spikes are still present but they are not confused for neuronal spikes.

FIG. 12 shows the analyses with the filter engaged. The waveforms demonstrated include only neuronal spikes and no artifact is noted. Note that the MER sample is the same as shown in FIG. 10; however, the artifact spikes are not registered, only the neuronal spikes as waveforms and in the raster.

The method (filter) is based on the observation that neuronal action potentials have two phases (FIG. 13) and that the half-height width of the first phase is small, typically less than 0.4 ms and the ratio of the half-height widths of the first to the second phase is less than 0.8 ms. The first half-height width of the first phase generally is greater than 0.4 ms and the ratio of the half-height width of the first phase to the second generally is greater than 0.8 ms (FIG. 14).

Thus, these two parameter, the half-height width of the first phase and the ratio of the half-height widths of the first and second phase can be used to differential artifact spikes from neuronal spikes.

Figure 13:
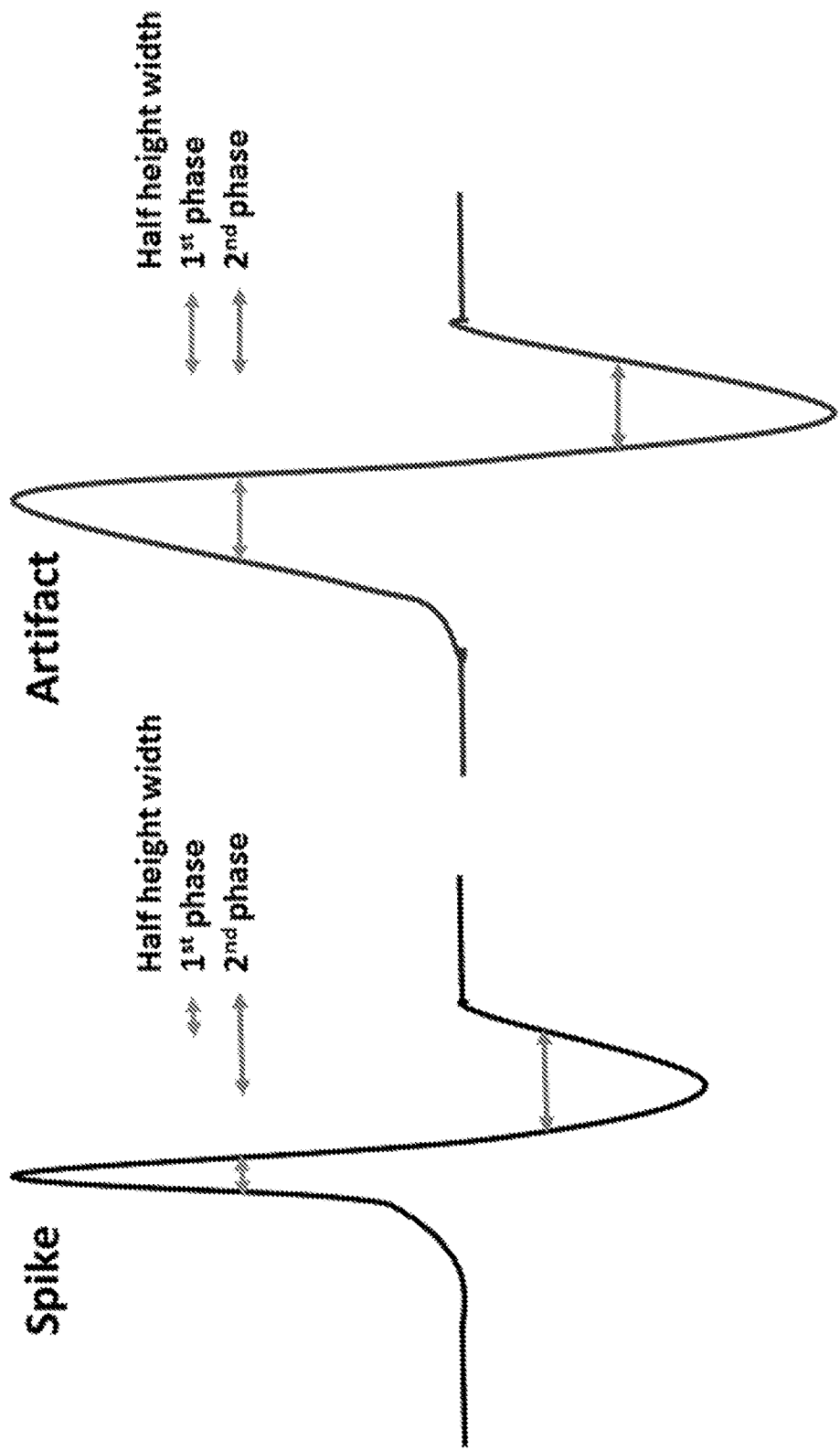
FIG. 13 shows a schematic representation of a neuronal spike (left) and artifact. The half-height is the width of the waveform at a height half of the maximum amplitude for each of the two phases. As can be seen, the half-height width of the first phase is shorter than that of the second phase for the neuronal spike which is not the case for the artifact. Thus, the ratio of the first to second half-height widths is less than 1 compared to those for artifact. Similarly, the half-height width of the first phase generally is shorter than that for artifact.

With specific reference to FIG. 13, shown is a schematic representation of a neuronal spike (left) and artifact (right). The half-height is the width of the waveform at a height half of the maximum amplitude for each of the two phases. As can be seen, the half-height width of the first phase is shorter than that of the second phase for the neuronal spike which is not the case for the artifact. Thus, the ratio of the first to second half-height widths is less than 1 compared to that for artifact. Similarly, the half-height width of the first phase generally is shorter than that for artifact.

Figure 14:
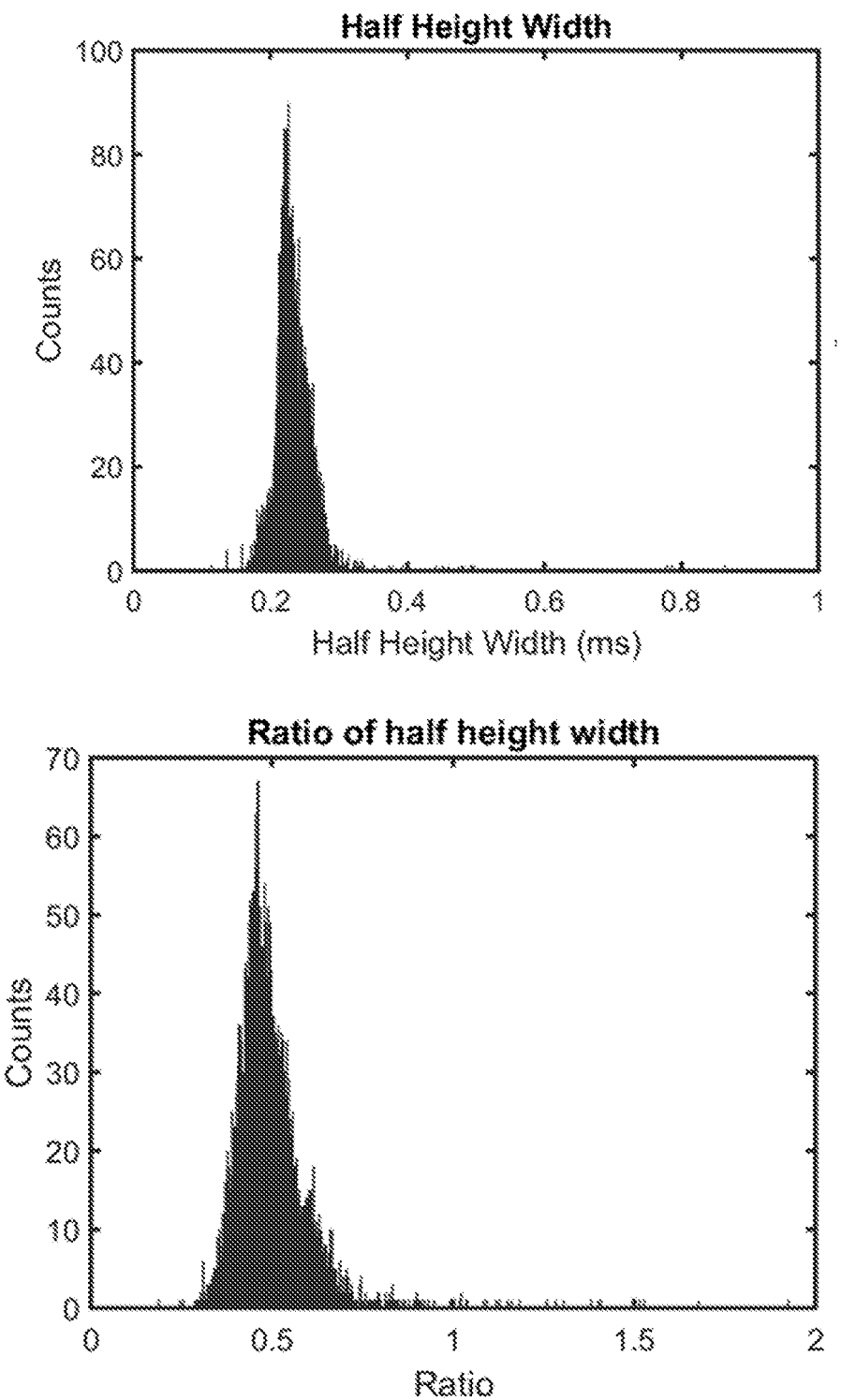
FIG. 14 shows interval incidence histograms for the half-height width of the first phase (left) for neurons pulled from recording in the ventral thalamus, globus pallidus interna, globus pallidus externa, subthalamic nucleus and substantia nigra pars compacta. On the right is the histogram showing the distributions of the ratio of the first to second phase half-height widths.

With specific reference to FIG. 14, shown are interval incidence histograms for the half-height width of the first phase (top) for neurons pulled from recording in the ventral thalamus, globus pallidus interna, globus pallidus externa, subthalamic nucleus, and substantia nigra pars compacta. On the bottom is the histogram showing the distributions of the ratio of the first to second phase half-height widths.

Figure 15:
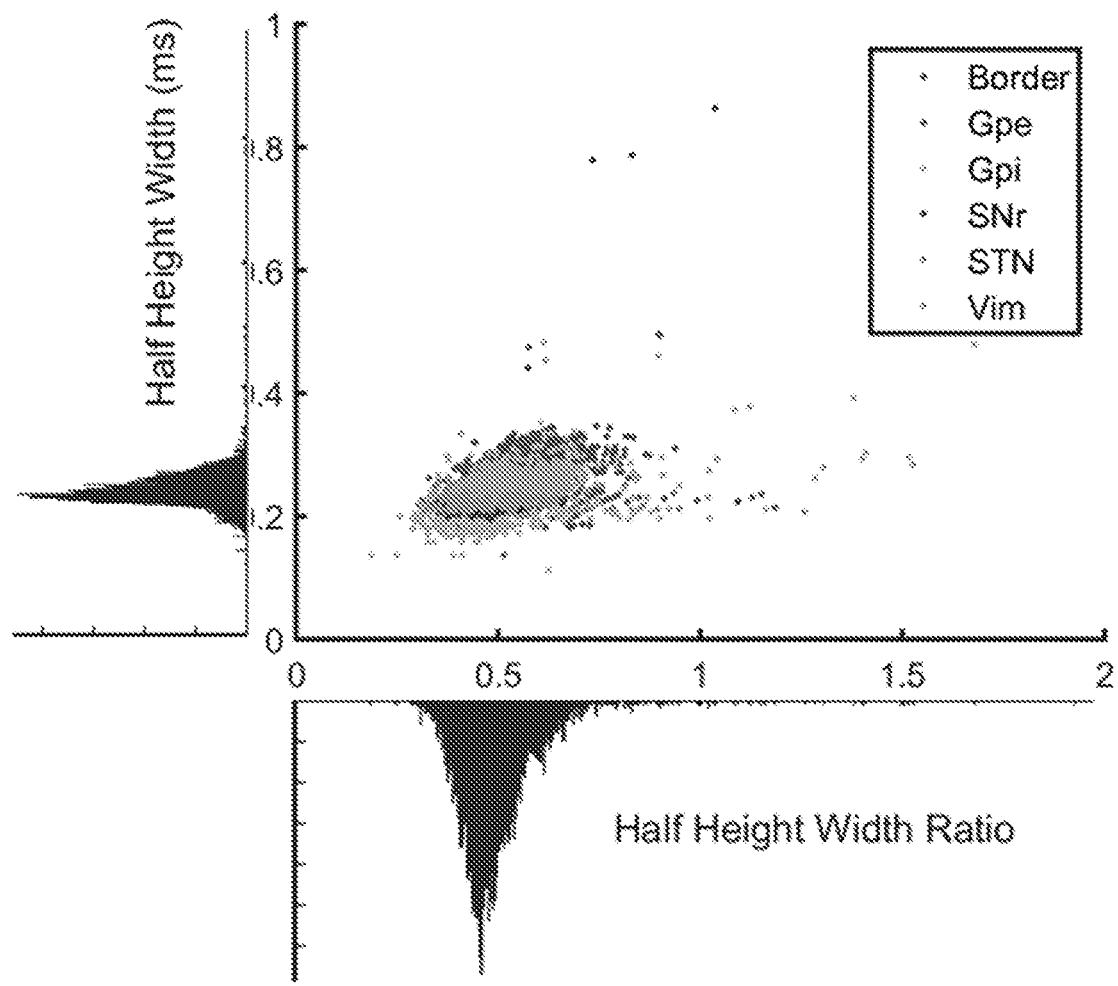
FIG. 15 shows two-dimensional plot of the half-height width of the first phase versus the ratio of first to second half-height widths for neurons recorded in the ventral intermediate nucleus of the thalamus (Vim), globus pallidus interna (Gpi), globus pallidus externa (Gpe), border cells, substantia nigra pars reticulata (SNr) and subthalamic nucleus (STN). Thus the spatial extent defined by the histograms in the vertical and horizontal axis can define the region of the two-dimensional space that contains data points associated with neuronal spikes. These boundaries can be defined by z-scores transformed from the distributions.

With reference to FIG. 15, shown is a plot of the first half-height wide versus the ratio of the first to the second half-height width for neurons recorded in the ventral intermediate nucleus of the thalamus (Vim), globus pallidus interna (Gpi), globus pallidus externa (Gpe), boarder cells, substantia nigra pars reticulata (SNr), and the subthalamic nucleus (STN). The distributions result in a two-dimensional cluster. Also, shown adjacent the vertical and horizontal axis are distributions of incidence histograms. Note that the distributions are Gaussian and thus, the distance of any signal data point for a single neuronal spike on each axis can be translated into a z-score. The boundaries to define the distribution along vertical and horizontal axis for neuronal spikes can be set by selection of an appropriate z-score indicating the probability that a data point belongs to the cluster that defines neuronal spikes. Data points outside those boundaries can be said to be artifact spikes.

Figure 16:
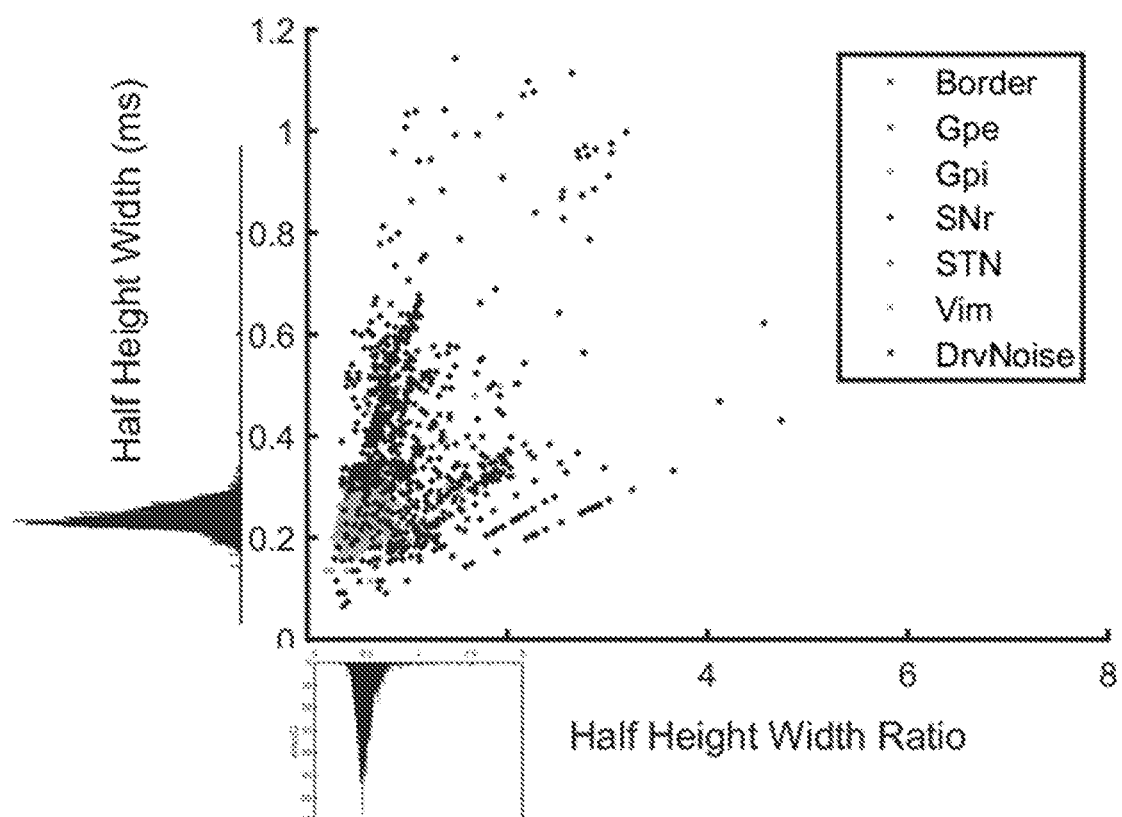
FIG. 16 shows two-dimensional plot of the half-height width of the first phase versus the ratio of first to second half-height widths for neurons recorded in the ventral intermediate nucleus of the thalamus (Vim), globus pallidus interna (Gpi), globus pallidus externa (Gpe), border cells, substantia nigra pars reticulata (SNr), subthalamic nucleus (STN) and artifact spikes from the micro-drive (DrvNoise). Thus the spatial extent defined by the histograms in the vertical and horizontal axis can define the region of the two-dimensional space that contains data points associated with neuronal spikes. These boundaries can be defined by z-scores transformed from the distributions. As can be readily appreciated, the data points, for a very large majority of the artifact spikes, lie outside the boundaries demarcating neuronal spikes.

FIG. 16, showing a two-dimensional plot of the half-height width of the first phase versus the ratio of first to second half-height widths for neurons recorded in the ventral intermediate nucleus of the thalamus (Vim), globus pallidus interna (Gpi), globus pallidus externa (Gpe), border cells, substantia nigra pars reticulata (SNr), subthalamic nucleus (STN), and artifact spikes from the micro-drive (DrvNoise), provides evidence that the large majority of artifact spikes from micro-drive artifact lie outside of the cluster defining the neuronal spikes. Thus the spatial extent defined by the histograms in the vertical and horizontal axis can define the region of the two-dimensional space that contains data points associated with neuronal spikes. These boundaries can be defined by z-scores transformed from the distributions.

Figure 17:
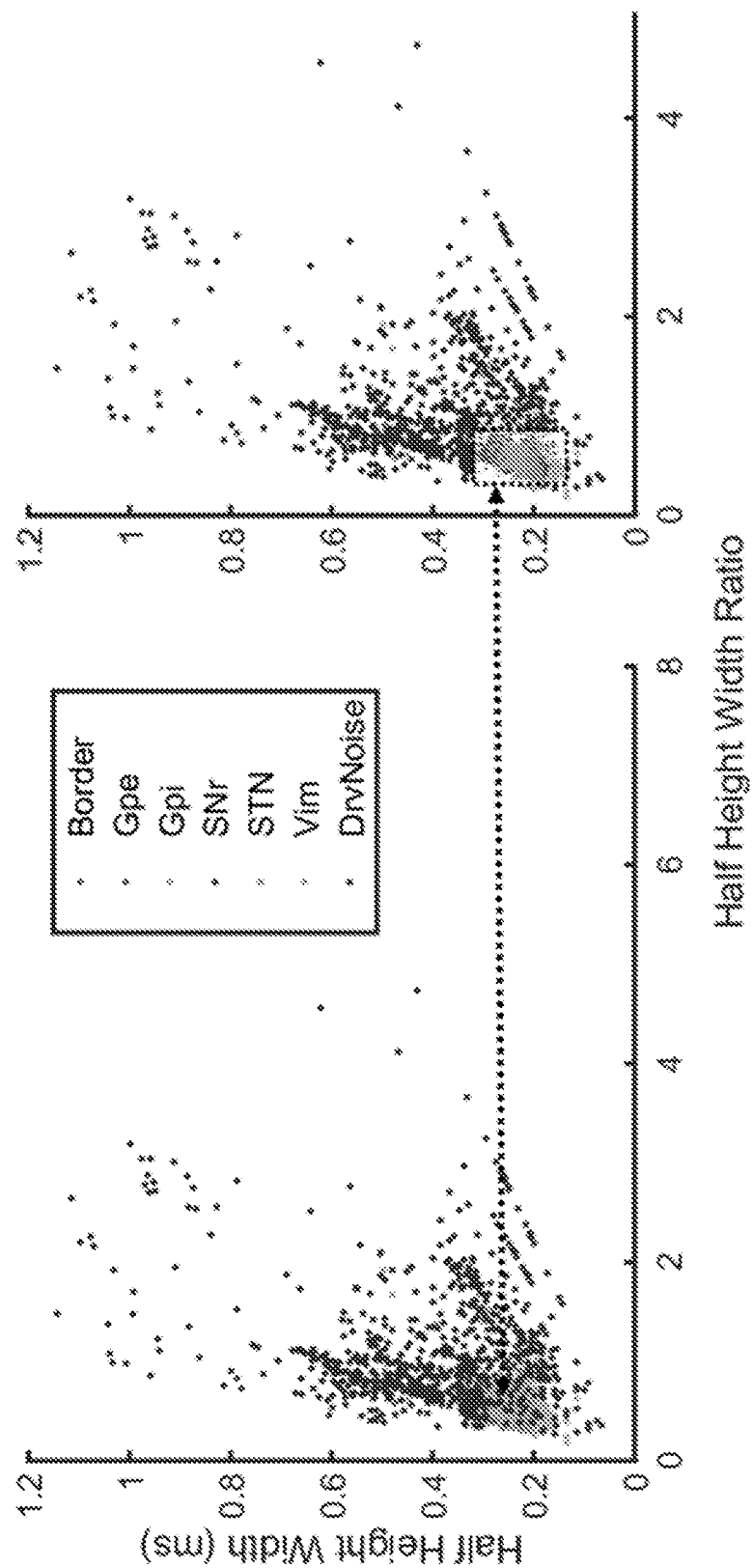
FIG. 17 shows two-dimensional plot of the half-height width of the first phase versus the ratio of first to second half-height widths for neurons recorded in the ventral intermediate nucleus of the thalamus (Vim), globus pallidus interna (Gpi), globus pallidus externa (Gpe), border cells, substantia nigra pars reticulata (SNr), subthalamic nucleus (STN) and artifact spikes from the micro-drive (DrvNoise) in panel (A). Panel (B) is the same as (A); however, the distribution of data points contained within the rectangle demarcating the extent along the vertical and horizontal axes from neurons is shown. As can be readily appreciated, the very large majority of artifact spikes associated with the micro-drive lie outside the box demarcating the neuronal spikes.

FIG. 17 shows the distribution of data points for both neuronal and artifact spikes. In the right-most plot, a rectangular box (broken lines) indicates the cutoffs along the vertical and horizontal axis. Data points within the box are defined as neuronal spikes while those outside the box are defined as artifact.

It is important to note that the method is not 100% specific, in that some artifact spikes are included within the box demarcating neuronal spikes. This is not a problem, as the primary purpose of the filter is to allow for "recording-on-the-fly" and thus, the methods need only have sufficient sensitivity and specificity to alert the user that neuronal spikes may be in the MER. At that point, the micro-drive can be stopped, thus stopping any artifact from the drive itself, and neuronal spikes can be detected with greater specificity and sensitivity sufficient for analysis and characterization of the recording site.

In accordance with the foregoing, provided herein are methods for localizing, targeting, and controlling a microelectrode. The method includes the step of advancing a microelectrode along a path within the brain of a patient. As used herein, the terms "electrode", and "microelectrode" refer to electrodes that are suitable for placement within a body to measure electrical potentials, for example, and without limitation local field potentials and evoked potentials. Such electrodes can be used in intracranial applications but are not limited to such purposes.

The microelectrode can be any microelectrode known to those of skill in the art for recording electrical potentials in the brain. However, the method is far more robust and useful when paired with the microelectrodes described herein. The method further includes the step of detecting, with at least one electrical contact of the microelectrode, electrical information, including two or more extracellular action potentials. In the case of a microelectrode with a number of electrical contacts arrayed along the long axis as described herein, the method can include analyzing electrical information and action potentials at each electrical contact, to provide great spatial resolution. These analyses can be automated, allowing for simultaneous analysis of any number of microelectrode contacts and rendering the use of multi-contact microelectrode arrays feasible which in turn greatly reduces operating time, cost, and risk to patients. The microelectrode is in communication, wired or wireless, with at least one processor, to communicate information about the extracellular action potentials, and other sensed electrical signals, to a processor.

As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11 and other radio frequency-based protocols and methods), analog transmissions, Global System for Mobile Communications (GSM), BLUETOOTH, ZigBee, EnOcean, TransferJet, Wireless USB, and the like known to those of skill in the art.

The method further includes the step of analyzing, with at least one processor, the extracellular action potentials over a time period. Analyzing the extracellular action potentials includes the steps of transforming the extracellular action potential information. In one aspect, the extracellular action potential information is transformed using circular statistic. That is, a processor transforms the extracellular potential information to a circle, with the time period forming the circumference of the circle. A processor then transforms the electrical information from the extracellular action potential information to two or more unit vectors extending outward from a perimeter of the circle. Based on the two or more unit vectors, a processor then calculates a resultant vector, the resultant vector having a length (r) and an angle (θ) dependent on the characteristics of the unit vectors. A processor then calculates a change in r and θ of the resultant vector over time. Based on these changes over time, a processor calculates power spectral density (PSD) peaks of the change in r and θ of the resultant vector over time. Such a calculation is performed using a peak detection algorithm, such as those known to those of skill in the art. Based on the PSD peaks, a processor then calculates a mean height of PSD peaks corresponding to change in r, and half-height widths of PSD peaks corresponding to change in r and change in angle.

Because each region of the brain will have a different electrical profile, that is, different profiles of bursting and non-bursting action potentials from the neuronal circuits within those areas of the brain, the mean height and half-height width information can be associated with a particular, precise localization of the microelectrode. This information is then stored in a database. In this way, it is possible to build a database that associates the information determined from the electrical signals with an anatomical location. Such a database, once generated, can then be used for automated targeting, control, and localization of microelectrodes, eliminating the need for, and drawbacks associated with, subjective interpretation of electrical signals from MERs.

Accordingly, also provided herein are methods for controlling a microelectrode. The method includes the step of advancing a microelectrode along a path within the brain of a patient. The step of advancing may occur through use of a Microdrive, for example, and without limitation, microdrives offered commercially by FHC, Inc. (Bowdoin, Me. USA) and AlphaOmega Co. USA, Inc. (Alpharetta, Ga. USA). The method further includes the step of detecting, with at least one electrical contact of the microelectrode, electrical information, including two or more extracellular action potentials. The microelectrode is in communication, wired or wireless, with at least one processor, to communicate information about the extracellular action potentials, and other sensed electrical signals, to a processor.

The method further includes the step of analyzing, with at least one processor, the extracellular action potentials over a time period. Analyzing the extracellular action potentials includes the steps of transforming the extracellular action potential information by transforming the extracellular potential information to a circle, with the time period forming the circumference of the circle. A processor then transforms the electrical information from the extracellular action potential information to two or more unit vectors extending outward from a perimeter of the circle. Based on the two or more unit vectors, a processor then calculates a resultant vector, the resultant vector having a length (r) and an angle (θ) dependent on the characteristics of the unit vectors. A processor then calculates a change in r and θ of the resultant vector over time. Based on these changes over time, a processor calculates power spectral density (PSD) peaks of the change in r and θ of the resultant vector over time. Such a calculation is performed using a peak detection algorithm, such as those known to those of skill in the art. Based on the PSD peaks, a processor then calculates a mean height of PSD peaks corresponding to change in r, and half-height widths of PSD peaks corresponding to change in r and change in angle.

The method further includes the steps of comparing the characteristics of the PSD peaks (mean height and half-height widths) with a database of PSD peak characteristics (mean height and half-height widths) associated with discrete anatomical locations. The software then advances or stops advancement of the microelectrode automatically based on the anatomical location in which the microelectrode is predicted to be embedded, based on the database comparison. Physician or clinician involvement can be limited merely to acting as a fail-safe, through use of a dead man's switch.

In another aspect of the method of localizing, targeting, and controlling a microelectrode, the microelectrode is advanced in a similar manner as described previously, and electrical signals/extracellular action potentials are detected as previously described. However, in another aspect, rather than circular statistics, analysis based on the concept of Brownian motion is utilized.

In such an aspect, the microelectrode is in communication (wired or wireless as described previously) with a processor, which receives electrical information from the microelectrode and analyzes the information. A processor determines an interval between two action potentials and calculates a mean interspike interval (ISI) based thereon. A processor then calculates an absolute value of a difference between the determined interval between two spikes and the mean ISI. A processor then normalizes the absolute value by dividing the absolute value by the number of ISIs measured. A processor then determines, based on the normalized absolute value.

Because each region of the brain will have a different electrical profile, that is, different profiles of bursting and non-bursting action potentials and, thus, different normalized absolute values, these values can be associated with a particular, precise localization of the microelectrode. This information is then stored in a database. In this way, it is possible to build a database that associates the information determined from the electrical signals with an anatomical location. Such a database, once generated, can then be used for automated targeting, control, and localization of microelectrodes, eliminating the need for, and drawbacks associated with, subjective interpretation of electrical signals from MERs.

Accordingly, also provided herein are methods for controlling a microelectrode. The method includes the step of advancing a microelectrode along a path within the brain of a patient. The step of advancing may occur through use of a Microdrive, for example, and without limitation, microdrives offered commercially by FHC, Inc. (Bowdoin, Me. USA) and AlphaOmega Co. USA, Inc. (Alpharetta, Ga. USA). The method further includes the step of detecting, with at least one electrical contact of the microelectrode, electrical information, including two or more extracellular action potentials. The microelectrode is in communication, wired or wireless, with at least one processor, to communicate information about the extracellular action potentials, and other sensed electrical signals, to a processor.

The microelectrode is in communication (wired or wireless as described previously) with a processor, which receives electrical information from the microelectrode and analyzes the information. A processor determines an interval between two action potentials and calculates a mean interspike interval (ISI) based thereon. A processor then calculates an absolute value of a difference between the determined interval between two spikes and the mean ISI. A processor then normalizes the absolute value by dividing the absolute value by the number of ISIs measured. A processor then determines, based on the normalized absolute value.

The method further includes the steps of comparing the normalized absolute value with a database of absolute values associated with discrete anatomical locations. The software then advances or stops advancement of the microelectrode automatically based on the anatomical location in which the microelectrode is predicted to be embedded, based on the database comparison. Physician or clinician involvement can be limited merely to acting as a fail-safe, through use of a dead man's switch.

These methods can be extended to any situation where extracellular action potentials are recorded and analyzed.

Clauses

Clause 1: A microelectrode comprising: a body comprising a proximal end, a distal end, and a sidewall there between defining a longitudinal axis, the body comprising an electrically non-conductive material and at least one portion comprising an electrically conductive material; and at least one electrochemical or biological biosensor disposed within or on the body.

Clause 2: The microelectrode of clause 1, wherein the at least one electrochemical or biological biosensor is an iron sensor.

Clause 3: The microelectrode of clause 2, wherein the iron sensor is an iron (II) or iron (III) sensor.

Clause 4: The microelectrode of clause 1, wherein the at least one electrochemical or biological biosensor is a hemoglobin sensor.

Clause 5: The microelectrode of any of clauses 1-4, wherein the at least one electrochemical or biological biosensor is at least two electrochemical or biological biosensors.

Clause 6: The microelectrode of clause 5, wherein the at least two electrochemical or biological biosensors are disposed along at least 1 mm of the longitudinal axis of the body, preferably at least 2 mm, more preferably at least 5 mm, most preferably at least 10 mm.

Clause 7: The microelectrode of any of clauses 1-6, wherein the microelectrode comprises a tip at the distal end.

Clause 8: The microelectrode of clause 7, wherein the tip is a frustoconical shape.

Clause 9: The microelectrode of clause 8 wherein the tip is a cone shape.

Clause 10: The microelectrode of any of clauses 7-9, wherein the at least one portion comprising an electrically conductive material is the tip.

Clause 11: The microelectrode of any of clauses 1-10, wherein the electrically non-conductive material is an organic or inorganic polymer, ceramic, or glass.

Clause 12: The microelectrode of any of clauses 1-11, wherein the electrically non-conductive material is glass.

Clause 13: The microelectrode of any of clauses 1-12, wherein the electrically conductive material is a metal or a carbon fiber material.

Clause 14: The microelectrode of any of clauses 1-13, wherein the electrically conductive material is at least one of stainless steel, aluminum, copper, graphite, platinum, gold, palladium, iridium, ruthenium, tungsten, alloys thereof, and combinations thereof.

Clause 15: The microelectrode of any of clauses 1-14, wherein the electrically conductive material is at least one of tungsten and a platinum-iridium alloy.

Clause 16: The microelectrode of any of clauses 1-12, wherein the electrically conductive material is an electrically conductive polymer.

Clause 17: The microelectrode of any of clauses 1-16, wherein the body comprises an electrically conductive material and the electrically non-conductive material is an insulating material covering substantially the entire body.

Clause 18: The microelectrode of clause 17, wherein the insulating material is a polyurethane or a polyimide.

Clause 19: A method of detecting the presence of a hematoma in a patient's brain during neurophysiological monitoring, comprising: advancing a microelectrode along a path within the brain of a patient, the microelectrode comprising a body comprising a proximal end, a distal end, and a sidewall therebetween defining a longitudinal axis, the body comprising an electrically non-conductive material and at least one portion comprising an electrically conductive material; and at least one electrochemical or biological biosensor disposed within or on the body; and detecting the presence or absence of a chemical or biological analyte, wherein the presence of the chemical or biological analyte is indicative of the presence of a hematoma.

Clause 20: The method of clause 19, wherein the at least one electrochemical or biological biosensor of the microelectrode is an iron sensor.

Clause 21: The method of clause 20, wherein the iron sensor is an iron (II) or iron (III) sensor.

Clause 22: The method of clause 19, wherein the at least one electrochemical or biological biosensor of the microelectrode is a hemoglobin sensor.

Clause 23: The method of any of clauses 19-22, wherein the at least one electrochemical or biological biosensor of the microelectrode is at least two electrochemical or biological biosensors.'

Clause 24: The method of clause 23, wherein the at least two electrochemical or biological biosensors are disposed along at least 1 mm of the longitudinal axis of the body, preferably at least 2 mm, more preferably at least 5 mm, most preferably at least 10 mm.

Clause 25: The method of any of clauses 19-24, further comprising advancing the electrode after detection of the chemical or biological analyte until the chemical or biological analyte is not detected, thereby providing an indication of the size of the hematoma.

Clause 26: A method of localizing a microelectrode within the brain of a patient, comprising: advancing a microelectrode according to any one of claims 1-18 along a path within the brain of a patient; detecting, with the microelectrode, two or more extracellular action potentials; analyzing, with at least one processor, the extracellular action potentials over a time period, wherein analyzing the extracellular action potentials comprises: transforming, with at least one processor, the time period to a circle; transforming, with at least one processor, the extracellular action potentials to unit vectors extending outward from a perimeter of the circle; calculating, with at least one processor, a resultant vector having a length (r) and an angle (θ), the length and angle dependent on the unit vectors; calculating, with at least one processor, a change in r and θ of the resultant vector over time; calculating, with at least one processor and using a peak detection algorithm, power spectral density (PSD) peaks of the change in r and θ of the resultant vector over time; calculating, with at least one processor, a mean height of PSD peaks corresponding to change in r and half-height widths of PSD peaks corresponding to change in r and change in angle; and determining, with at least one processor and based on the mean height and half-height widths, an anatomical location of the microelectrode; and storing, in a database, the mean height, half-height widths, and anatomical location.

Clause 27: A microelectrode comprising: a body comprising a proximal end, a distal end, and a sidewall there between defining a longitudinal axis, the body comprising an electrically non-conductive material; and at least one electrical contact comprising an electrically conductive material, said electrical contact embedded in a cavity in the sidewall of the body and configured such that the electrical contact does not protrude radially beyond the perimeter of the body.

Clause 28: The microelectrode of clause 27, wherein the electrical contact is a conical shape.

Clause 29: The microelectrode of clause 27 or clause 28, wherein the electrical contact occupies less than the entirety of the cavity in the sidewall.

Clause 30: The microelectrode of clause 28 or clause 29, wherein the remaining space in the cavity is filled with a porous material.

Clause 31: The microelectrode of clause 30, wherein the porous material is a cotton fiber, glass sponge, ceramic, gel, plastic, or collodion.

Clause 32: The microelectrode of clause 30 or clause 31, wherein the porous material is wetted with a conductive substance.

Clause 33: The microelectrode of clause 32, wherein the conductive substance is physiological saline, other biologically compatible solution containing ions, or artificial cerebrospinal fluid.

Clause 34: The microelectrode of clause 27, wherein the electrical contact is embedded in a non-conductive material that extends radially outward from the body of the microelectrode.

Clause 35: The microelectrode of any one of clauses 27-34, wherein the microelectrode further comprises one or more sensors for detecting hemoglobin or iron.

Clause 36: A method of localizing a microelectrode within the brain of a patient, comprising: advancing a microelectrode according to any one of clauses 1-18 or 27-35 along a path within the brain of a patient; detecting, with the at least one electrical contact of the microelectrode, two or more extracellular action potentials; analyzing, with at least one processor, the extracellular action potentials over a time period, wherein analyzing the extracellular action potentials comprises: transforming, with at least one processor, the time period to a circle; transforming, with at least one processor, the extracellular action potentials to unit vectors extending outward from a perimeter of the circle; calculating, with at least one processor, a resultant vector having a length (r) and an angle (θ), the length and angle dependent on the unit vectors; calculating, with at least one processor, a change in r and θ of the resultant vector over time; calculating, with at least one processor and using a peak detection algorithm, power spectral density (PSD) peaks of the change in r and θ of the resultant vector over time; calculating, with at least one processor, a mean height of PSD peaks corresponding to change in r and half-height widths of PSD peaks corresponding to change in r and change in angle; and determining, with at least one processor and based on the mean height and half-height widths, an anatomical location of the microelectrode; and storing, in a database, the mean height, half-height widths, and anatomical location.

Clause 37: A method of localizing a microelectrode within the brain of a patient, comprising: advancing a microelectrode according to any one of clauses 1-18 or 27-35 along a path within the brain of a patient, the microelectrode in communication with at least one processor detecting, with the at least one electrical contact of the microelectrode, two or more extracellular action potentials; analyzing, with at least one processor, the extracellular action potentials over a time period, wherein analyzing the extracellular action potentials comprises: determining, with at least one processor, an interval between two action potentials; calculating, with at least one processor and based on the determined interval, a mean interval between action potentials; calculating, with at least one processor, an absolute value of a difference between the determined interval and the mean interval; normalizing, with at least one processor, the absolute value; and determining, with at least one processor and based on the normalized absolute value, an anatomical location of the microelectrode; and storing, in a database, the normalized absolute value and anatomical location of the microelectrode.

The preceding description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the preceding will fall within the scope of the appended claims. The present invention should not be considered limited to the presently disclosed aspects, whether provided in the examples or elsewhere herein.

The invention claimed is:

1. A microelectrode comprising:
    a body comprising a proximal end, a distal end comprising a cone-shaped tip, and a sidewall there between defining a longitudinal axis, the body comprising an electrically non-conductive material and at least one electrical contact comprising an electrically conductive material; and
    at least one electrochemical biosensor disposed within or on the body;
    wherein the at least one electrochemical biosensor is a hemoglobin sensor configured to detect the presence of hemoglobin, and
    wherein the electrical contact is embedded in a non-conductive material or insulating material that slopes radially outward from the body of the microelectrode.

2. The microelectrode of claim 1, wherein the at least one electrochemical biosensor is at least two electrochemical biosensors.

3. The microelectrode of claim 2, wherein the at least two electrochemical biosensors are disposed along at least 1 mm of the longitudinal axis of the body.

4. The microelectrode of claim 1, wherein the electrically non-conductive material is an organic or inorganic polymer, ceramic, or glass.

5. The microelectrode of claim 1, wherein the electrically non-conductive material is glass.

6. The microelectrode of claim 1, wherein the electrically conductive material is a metal or a carbon fiber material.

7. The microelectrode of claim 1, wherein the electrically conductive material is at least one of stainless steel, aluminum, copper, graphite, platinum, gold, palladium, iridium, ruthenium, tungsten, alloys thereof, and combinations thereof.

8. The microelectrode of claim 1, wherein the electrically conductive material is at least one of tungsten and a platinum-iridium alloy.

9. The microelectrode of claim 1, wherein the electrically conductive material is an electrically conductive polymer.

10. The microelectrode of claim 1, wherein the body comprises an electrically conductive material and the electrically non-conductive material is an insulating material covering substantially the entire body.

11. The microelectrode of claim 10, wherein the insulating material is a polyurethane or a polyimide.

12. The microelectrode of claim 1, wherein the electrical contact comprises a conical shape.

13. The microelectrode of claim 1, wherein the non-conductive material or insulating material form a recess, wherein said recess is partially filled with a porous material wetted with a conductive substance.

14. The microelectrode of claim 1, wherein a plurality of electrical contacts are arranged along the longitudinal axis.

15. A method of detecting the presence of a hematoma in a patient's brain during neurophysiological monitoring, comprising:
- advancing a microelectrode along a path within the brain of a patient, the microelectrode comprising:
  - a body comprising a proximal end, a distal end comprising a cone-shaped tip, and a sidewall therebetween defining a longitudinal axis, the body comprising an electrically non-conductive material and at least one electrical contact comprising an electrically conductive material; and
  - at least one electrochemical biosensor disposed within or on the body;
  - wherein the at least one electrochemical biosensor is a hemoglobin sensor configured to detect the presence of hemoglobin, and
  - wherein the electrical contact is embedded in a non-conductive material or insulating material that slopes radially outward from the body of the microelectrode; and
- detecting the presence or absence of a chemical or biological analyte, wherein the presence of the chemical or biological analyte is indicative of the presence of a hematoma.

16. The method of claim 15, wherein the at least one electrochemical biosensor of the microelectrode is at least two electrochemical biosensors.

17. The method of claim 16, wherein the at least two electrochemical biosensors are disposed along at least 1 mm of the longitudinal axis of the body.

18. The method of claim 15, further comprising advancing the electrode after detection of the chemical or biological analyte until the chemical or biological analyte is not detected, thereby providing an indication of the size of the hematoma.

* * * * *